(12) United States Patent
Kung

(10) Patent No.: US 6,212,430 B1
(45) Date of Patent: Apr. 3, 2001

(54) ELECTROMAGNETIC FIELD SOURCE WITH DETECTION OF POSITION OF SECONDARY COIL IN RELATION TO MULTIPLE PRIMARY COILS

(75) Inventor: Robert T. V. Kung, Andover, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/304,198

(22) Filed: May 3, 1999

(51) Int. Cl.$^7$ .................................................. A61N 1/02
(52) U.S. Cl. ................................................................ 607/61
(58) Field of Search ................................. 607/32–34, 30, 607/60, 61; 128/903

(56) References Cited

U.S. PATENT DOCUMENTS

| | | |
|---|---|---|
| 3,195,038 | 7/1965 | Fry . |
| 3,711,747 | 1/1973 | Sahara et al. . |
| 3,825,925 | 7/1974 | Drusch . |
| 3,867,950 | 2/1975 | Fischell . |
| 3,995,137 | 11/1976 | Okada et al. . |
| 4,011,499 | 3/1977 | Betsill et al. . |
| 4,134,408 * | 1/1979 | Brownlee et al. ................. 607/33 |
| 4,673,888 | 6/1987 | Engelmann et al. . |
| 4,678,986 | 7/1987 | Barthelemy . |
| 4,716,353 | 12/1987 | Engelmann . |
| 4,717,889 | 1/1988 | Engelmann . |
| 4,741,339 | 5/1988 | Harrison et al. . |
| 4,808,924 | 2/1989 | Cecco et al. . |
| 4,837,497 | 6/1989 | Leibovich . |
| 5,314,453 | 5/1994 | Jeutter . |
| 5,355,296 | 10/1994 | Kuo et al. . |

(List continued on next page.)

FOREIGN PATENT DOCUMENTS

| | | | |
|---|---|---|---|
| 9729802 | 8/1997 | (WO) .............................. A61N/1/375 |
| 9747065 | 12/1997 | (WO) .............................. H02J/5/00 |
| 9944684 | 9/1999 | (WO) .............................. A61N/1/378 |

OTHER PUBLICATIONS

Ahn et al., In Vivo Performance Evaluation of a Transcutaneous Energy and Information Transmission System for the Total Artificial Heart, ASAIO Journal 1993, M208–M212.

H. Matsuki et al., Signal Transmission for Implantable Medical Devices using Figure–of–eight Coils, IEEE Transactions on Magnetics vol. 32 No. 5, Sep., 1996.

*Primary Examiner*—George R. Evanisko
(74) *Attorney, Agent, or Firm*—Nutter, McClennen & Fish, LLP; Thomas J. Engellenner, Esq; Ronald E. Cahill, Esq.

(57) ABSTRACT

An electromagnetic field source (EFS) for providing electromagnetic energy to a secondary coil, including two or more primary coils that each carry a time-varying current to produce an electromagnetic field, and a controller that selectively provides current to one or more primary coils based on their position with respect to the secondary coil. The secondary coil may be implanted in a human recipient and used to provide power for the operation of a medical device, such as an artificial heart or ventricular assist device. The invention also provides such a secondary coil and EFS, collectively referred to as a transcutaneous energy transfer (TET) device. The primary coils of the EFS or TET may be housed in furniture. For example, they may be housed in a bed mattress or mattress pad on which the recipient rests, or in a blanket for covering the recipient. The controller includes a proximity detector that identifies those primary coils that are closest to the secondary coil, and a current director that, responsive to the proximity detector, selectively directs time-varying currents through the closest primary coils. The controller may also include an orientation detector, coupled to the current director, that determines an orientation of the secondary coil with respect to the closest primary coils. In one implementation, the proximity detector identifies the quantity of closest primary coils utilizing a resonance frequency shift detector that detects a shift in inductance of one or more primary coils due to the proximity of the secondary coil.

98 Claims, 11 Drawing Sheets

U.S. PATENT DOCUMENTS 5,506,503  4/1996  Cecco et al. .
5,741,316  4/1998  Chen et al. .
5,755,748  5/1998  Borza .
6,047,214 * 4/2000  Mueller et al. ........................ 607/61

* cited by examiner

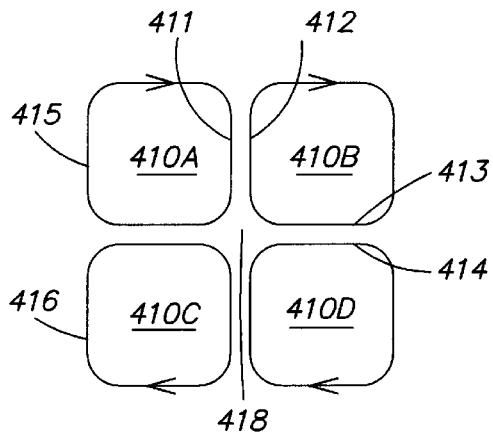
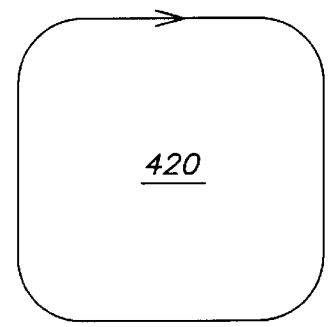
FIG. 4A
FIG. 4B
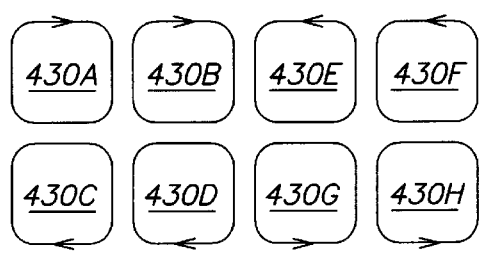
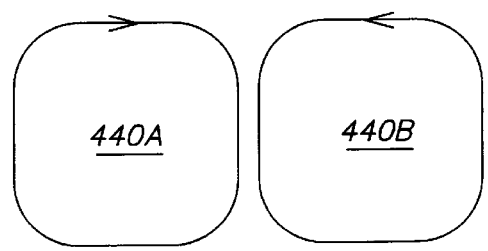
FIG. 4C
FIG. 4D

ELECTROMAGNETIC FIELD SOURCE WITH DETECTION OF POSITION OF SECONDARY COIL IN RELATION TO MULTIPLE PRIMARY COILS

BACKGROUND OF THE INVENTION

1. Field of the Invention

This invention relates generally to energy transfer devices and methods and, more particularly, to devices and processes for transcutaneous energy transfer (TET) to a secondary coil implanted in a subject.

2. Related Art

Many medical devices are now designed to be implanted in humans or animals, including pacemakers, defibrillators, circulatory assist devices, cardiac replacement devices such as artificial hearts, cochler implants, neuromuscular simulators, biosensors, and the like. Since many of these devices require a source of power, inductively coupled transcutaneous energy transfer (TET) systems are coming into increasing use. A TET system may be employed to supplement, replace, or charge an implanted power source, such as a rechargeable battery. Unlike other types of power transfer systems, TET systems have an advantage of being able to provide power to the implanted electrical and/or mechanical device, or recharge the internal power source, without puncturing the skin. Thus, possibilities of infection are reduced and comfort and convenience are increased.

TET devices include an external primary coil and an implanted secondary coil, separated by intervening layers of tissue. The two coils constitute a transcutaneous transformer. The transformer is designed to induce alternating current in the subcutaneous secondary coil, typically for transformation to direct current to power the implanted device. TET devices therefore also typically include an oscillator and other electrical circuits for periodically providing appropriate alternating current to the primary coil. These circuits, referred to for convenience herein as "TET primary circuits," receive their power from an external power source.

Generally, the non-implanted portions of conventional TET systems are attached externally to the patient, typically by a belt or other fastener or garment, such that the primary coil of the TET is operationally aligned with the implanted secondary coil. The TET primary circuits and external power supply are also generally attached to the patient's body at or near the site of the attachment of the primary coil. Such a configuration typically is disadvantageous, however, particularly when the patient is sleeping or resting. For example, if a patient is sleeping on a mattress, the patient would likely be uncomfortable, or restricted in movement, if all or some of the TET primary circuits and external power supply were attached to the patient. In addition to discomfort or restriction of movement, additional disadvantages of such body attachments include possibilities of injury to the patient or the devices. Movements of the patient may alter the position of the primary coil so that it is not properly positioned over the implanted secondary coil to achieve a desired or required transfer of power.

To overcome these drawbacks, other conventional approaches require only the primary coil be attached to the patient. Wires connect the primary coil to the TET primary circuits, which, with the power supply, may be located at a distance from the patient outside of the sleeping or resting surface. However, such an alternative configuration also has significant disadvantages. First, the primary coil is still attached to the patient and therefore subject to the above drawbacks may cause discomfort or restriction of movement. Also, as the patient moves, the wires connecting the externally attached primary coil to the TET primary circuits may become tangled or entangled with bedding or the patient. In addition to being uncomfortable, such tangling may result in dislodging the primary coil from its required alignment; it may injure the patient, such as by restricting blood or oxygen supply; or it may interfere with tubes or other devices attached to the patient.

SUMMARY

To overcome the above and other drawbacks to conventional systems, the present invention provides an electromagnetic field source (EFS) for providing electromagnetic energy to a secondary coil. In one embodiment, the EFS includes two or more primary coils that each carry a time-varying current to produce an electromagnetic field. The EFS also includes a controller that selectively provides current to one or more of the primary coils based on their position relative to the secondary coil. The controller may be implemented in electrical circuits, software, firmware, or any combination thereof.

In another embodiment, the invention provides a transcutaneous energy transmission (TET) device including a secondary coil implanted in a human being. In this embodiment, the secondary coil is used to provide power for the operation of an implanted medical device, such as an artificial heart or ventricular assist device. In some implementations, the primary coils are housed in furniture, such as a bed mattress. Also, the primary coils may be housed in bed covering, such as a blanket or mattress pad.

In certain embodiments the controller includes a proximity detector that identifies a quantity of primary coils that are closest to the secondary coil, referred herein to as the "closest" primary coils. A current director that is responsive to the proximity detector is also included in the controller. The current director selectively directs time-varying currents through the closest primary coils.

One advantage of a TET in accordance with certain aspects of the present invention is that there are no wires connecting the subject of the implanted device to external components, such as a power supply or other electrical circuits. Rather, a recipient of the implanted device may rest on furniture that houses the primary coils, and those primary coils that are closest to the implanted secondary coil may be energized. Thus, the recipient is uninhibited with respect to movement on or in the furniture, such as a bed, couch, or chair, and is provided with a more comfortable resting environment. Also, serious disadvantages of known systems, such as becoming entangled with a wire, or of dislodging a primary coil, are avoided by the present invention.

Another advantage is the portability of implementations such as those in which the primary coils are housed in a bed covering or a mattress pad. Thus, a recipient may pack such housing, together with the controller and power supply, in suitcases or similar containers for traveling. Similarly, a hospital mattress may readily be converted to include portions of a TET by covering it with a blanket or mattress pad containing primary coils in accordance with embodiments of the present invention.

Advantageously, the primary coils may be disposed over substantially all of the top surface of the mattress, or throughout the bed covering or mattress pad. Thus, in such embodiments, if the recipient shifts position on the mattress, there will be one or more primary coils located close to the implanted secondary coil. In some implementations, the primary coils may be positioned in generally even rows and columns with respect to the top surface of the mattress. In other implementations, they may be positioned generally in hexagonal arrangements. It will be understood to those of ordinary skill that there are many possible configurations that provide primary coils over the entire surface upon which the recipient is resting or reclining.

Also advantageously, the controller of the EFS or TET may determine the approximate distance between the primary coils and the secondary coil, and adjust the amount of current to the closest primary coils accordingly. In particular, a proximity detector may be included to determine an approximate distance between one or more of the closest primary coils and the secondary coil. In embodiments that include such a proximity detector, if that distance is greater than a nominal threshold value, current director may increase the currents through selected ones of the closest primary coils. For example, if the recipient is sleeping on a pillow or is otherwise raised above the mattress, the distance from the implanted secondary coil to the primary coils in the mattress may be greater than normal (i.e., greater than when the recipient is sleeping directly on the mattress). By increasing the amount of current directed to the closest primary coils, the electromagnetic fields of the closest primary coils are increased to reach the secondary coil so that it may provide power to the medical device or to an energy storage device. In one embodiment of the EFS or TET, the proximity detector identifies a predetermined number of the closest primary coils. Alternatively, the quantity of closest primary coils may be identified by the proximity detector based on the size of the secondary coil.

The primary coils may be disposed in their housings in accordance with a wide variety of geometric schemes or arrangements. For example, the primary coils may be disposed in a single plane, or in two or more parallel planes. It should be understood that the specification herein of this, and other, geometric arrangements may be approximate. For example, it generally is not required that the primary coils be disposed precisely in a single or parallel planes, in precisely a square pattern, and so on. Rather, they may be approximately so disposed. Similarly, a second-layer primary coil need not be precisely aligned with first-layer primary coils, as described below.

In one embodiment in which a configuration of two parallel planes is used, dead zones of electromagnetic fields generated by one or more primary coils of a first plane are encompassed by electromagnetic fields generated by primary coils in a second plane that is parallel to the first plane. The term "dead zone" is used herein to refer to a space in which an electromagnetic field generated by a primary coil is not effective in energizing a secondary coil disposed in that space. This term is further explained, and is illustrated, below. The word "energize," and its grammatical variants, is used herein to refer to the provision of current to a primary coil so that it produces an electromagnetic field. The word "encompassed" is used herein in this context to refer to the covering of the dead zone by the electromagnetic field of a second layer of primary coils, such that the electromagnetic field is effective in energizing the secondary coil disposed in the dead zone of a first layer of primary coils.

In some embodiments having primary coils disposed in two parallel planes, a first plane includes two or more mutually adjacent first-plane primary coils. The term "mutually adjacent" means that each of two or more primary coils in a group is adjacent to each of the other primary coils in that group. Examples of such arrangements are the placement of the centers of the primary coils at the corners of a rectangular or triangular shape in the first plane. In such embodiments, a second plane is provided that has at least one second-plane primary coil (not to be confused with a secondary coil). These coils are positioned so that the projection of a magnetic center of the second-plane primary coil on the first plane is approximately equidistant from magnetic centers of each of the two or more mutually adjacent first-plane primary coils. For example, if first-plane square primary coils are positioned so that their corners are adjacent to each other, then a second-plane primary coil is placed in the second plane such that the projection of its magnetic center onto the first plane aligns with the corners of the first-plane square. The term "magnetic center" of a coil is used herein to mean the geometric center of iso-magnetic contours representing the magnetic field generated by the coil. In a particular implementation of such an arrangement, the first plane has four mutually adjacent primary coils positioned in a roughly square arrangement. The second plane has one primary coil positioned so that the projection of its geometric center on the first plane is approximately centrally located among the four first-plane primary coils.

In some embodiments, the EFS or TET also includes an orientation detector, coupled to the current director, that determines the orientation of the plane of the secondary coil with respect to the planes of the closest primary coils. In some implementations, the orientation detector is electrically coupled to the primary coils and determines the orientation of the plane of the secondary coil utilizing a resonance frequency shift detector. The detector compares shifts in inductance of two or more primary coils due to the proximity of the secondary coil. In other implementations, the orientation detector may determine the plane of the secondary coil utilizing an optical sensor, a mechanical sensor, electromagnetic transmission, or any combination of these or other sensors now or later developed.

In some embodiments, if the orientation detector determines that the secondary coil is disposed in a plane predominantly parallel to the planes of the closest primary coils, the current director directs time-varying currents to flow through the closest primary coils so that each current flows in the same direction. In one implementation of such an embodiment, the quantity of closest primary coils may be simple one coil. In particular, there may be a single closest primary coil if the proximity detector determines that the secondary coil is proximate to an electromagnetic field of the one closest primary coil, not including a dead zone. In another implementation, the quantity of closest primary coils is two or more when all of the primary coils are disposed in the same plane and the proximity detector determines that the secondary coil is proximate to a dead zone of the one closest primary coil.

If the orientation detector determines that the secondary coil is disposed in a plane predominantly perpendicular to the planes of the closest primary coils, the current director directs time-varying currents to flow through the closest primary coils so that a current in each closest primary coil flows in a direction opposite to a direction of a current in an adjacent closest primary coil. In one implementation in which the secondary coil is perpendicularly positioned, the quantity of closest primary coils is two.

The EFS may also include a power supply that is coupled to the controller and that provides current to the primary coils. It should be understood that the power supply may not be directly coupled to the primary coils, but that intermediary components, such as a regulator, may be present. Alternatively, the regulator or other components may be included in the power supply.

In further embodiments, the invention provides a method for providing electromagnetic energy to a secondary coil. The method includes disposing primary coils, each constructed and arranged to carry a time-varying current to produce an electromagnetic field, and selectively providing current to the primary coils based on their position with respect to the secondary coil. In some implementations, such selection includes identifying a quantity of the primary coils that are closest to the secondary coil, and selectively directing time-varying currents through the closest primary coils.

In other embodiments, the invention is a cardiac-assist device including pumping means and a transcutaneous energy transmission (TET) device. The TET includes a secondary coil implanted in a subject, primary coils that carry a time-varying current to produce an electromagnetic field, and a controller that selectively provides current to one or more of the primary coils based on their position with respect to the secondary coil. The pumping means may include a total artificial heart or a ventricular assist device. More generally, the invention provides in some embodiments an organ-assist device including such a TET and an internally implanted organ-assist component.

In yet further embodiments, the invention is an article of furniture having embedded in it two or more primary coils that each carry a time-varying current to produce an electromagnetic field. The furniture also includes a controller that selectively provides current to one or more of the primary coils based on their position with respect to the secondary coil.

Further features and advantages of the present invention as well as the structure and operation of various embodiments of the present invention are described in detail below with reference to the accompanying drawings. In the drawings, like reference numerals indicate identical or functionally similar elements. Additionally, the left-most one or two digits of a reference numeral identifies the drawing in which the reference numeral first appears.

BRIEF DESCRIPTION OF THE DRAWINGS

The above and further advantages of the invention will be more clearly appreciated from the following detailed description when taken in conjunction with the accompanying drawings. In the drawings like reference numerals indicate like structures or method steps, in which the left-most one or two digits of a reference numeral indicates the number of the figure in which the referenced element first appears (for example, the element 210 appears first in FIG. 2, the element 1010 first appears in FIG. 10). In the Figures:

FIG. 4A is a schematic top view of four primary coils arranged in a generally square-shape pattern and having the same direction of current flow, such as may be employed in an exemplary embodiment of the electromagnetic field source of FIG. 1;

FIG. 4B is a schematic top view of one embodiment of a primary coil that generates a magnetic field generally equivalent to the magnetic fields generated by the primary coils of FIG. 4A;

FIG. 4C is a schematic top view of eight primary coils arranged in two adjacent square-shape patterns, the coils of one pattern having opposite directions of current flow from the coils of the other pattern, such as may be employed in an exemplary embodiment of the electromagnetic field source of FIG. 1;

FIG. 4D is a schematic top view of one embodiment of two adjacent primary coils that generate a combined magnetic field generally equivalent to the magnetic fields generated by the primary coils of FIG. 4C;

DETAILED DESCRIPTION

I. Introduction

The attributes of the present invention and its underlying method and architecture will now be described in greater detail in reference to one embodiment of the invention, referred to as an electromagnetic field source (EFS) 100, aspects of which are represented in FIGS. 1 through 10. In this detailed description, references are made to various functional modules of the present invention that may be implemented using software, hardware including electronic circuits, firmware, or any combination thereof. Some of these implementations may also include a microprocessor (not shown) to execute the software or firmware in accordance with techniques well known to those skilled in the relevant arts. Such a microprocessor may be one of a variety of known types, or a microprocessor to be developed in the future.

Figure 1:
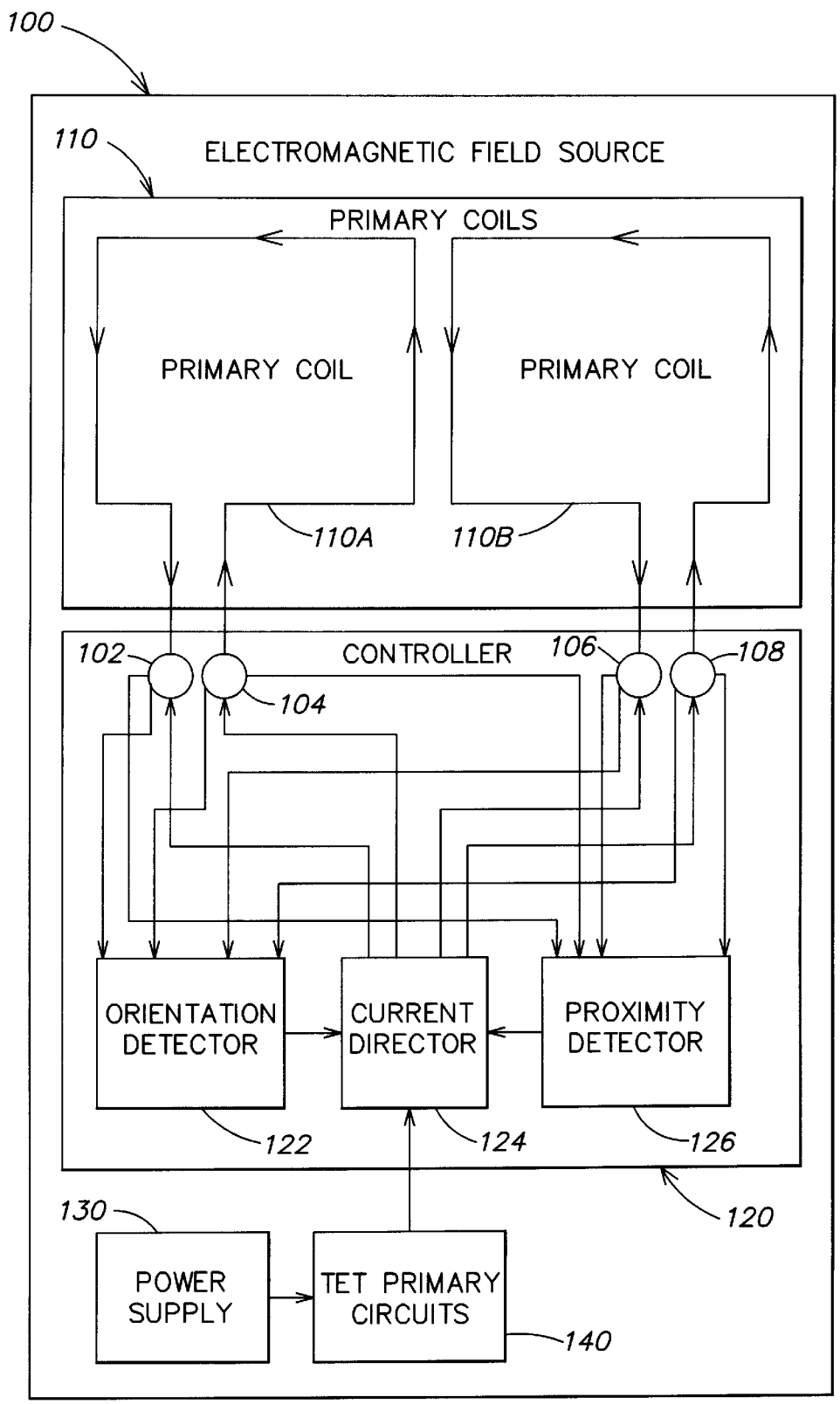
FIG. 1 is a schematic and functional block diagram of an electromagnetic field source in accordance with one embodiment of the present invention.

FIG. 1 is a schematic and functional block diagram of EFS 100 suitable for implementation in a transcutaneous energy transfer (TET) system. EFS 100 primarily includes primary coils 110A and 110B (collectively and generally referred to as primary coils 110) and a controller 120. As shown in FIG. 1 EFS 100 is connected to TET primary circuits 140 and a power supply 130. Primary coils 110 generate electromagnetic fields for providing energy to a secondary coil that, in this exemplary embodiment, is implanted in a human recipient. Controller 120 selectively provides current to one or more of primary coils 110 based on a number of factors such as the relative position and orientation of the primary and secondary coils, the configuration of the coils, the power to be transferred, the magnitude of the current, among others. Such factors are determined by the application of the invention and the manner in which the invention is implemented, as described in detail below.

Figure 2:
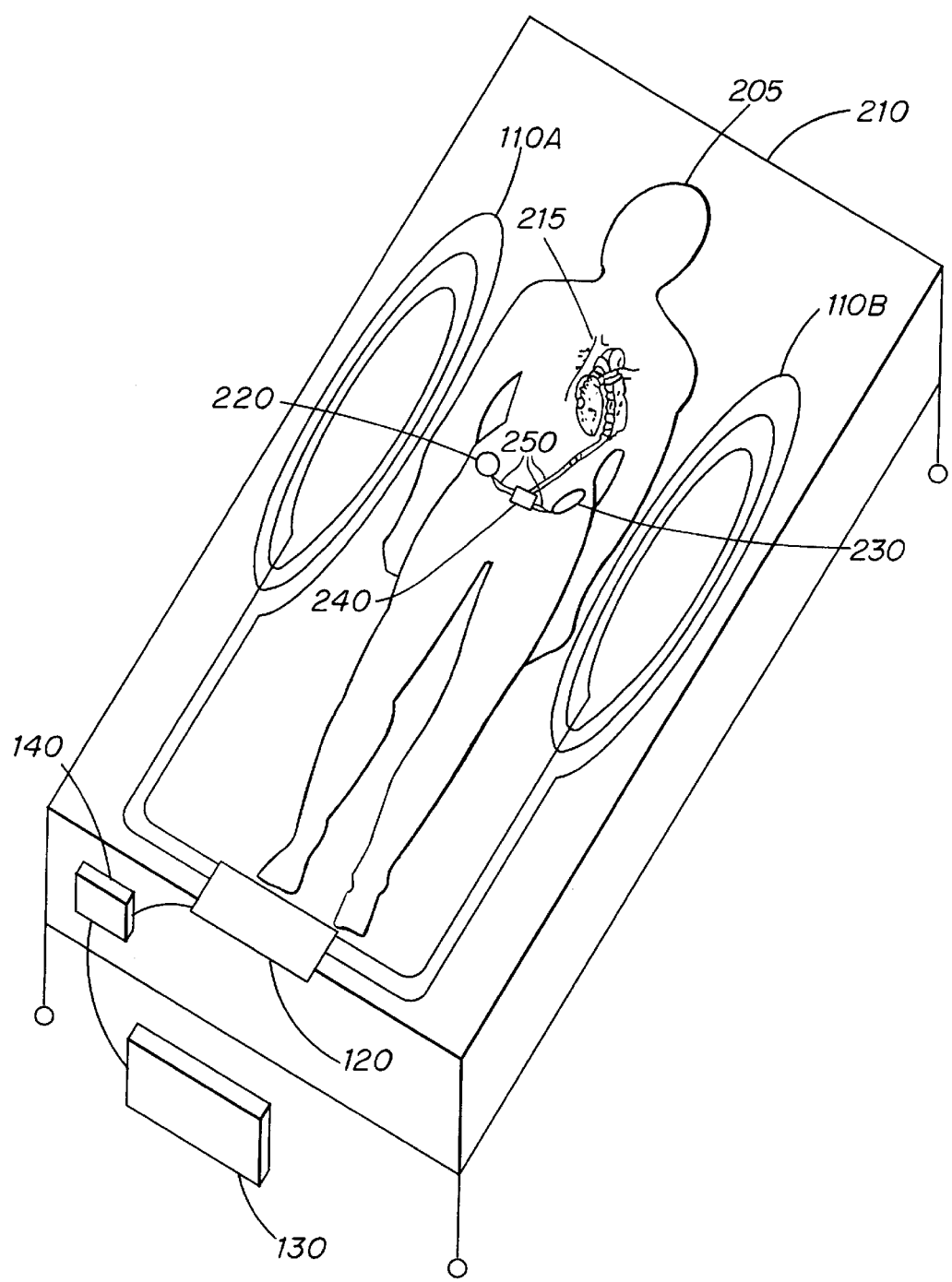
FIG. 2 is a schematic cross-sectional top view of a secondary coil and associated components, including an artificial heart, implanted in a recipient reclining on a mattress having embedded therein the electronic field source of FIG. 1.

A particular implementation of EFS 100 for use as part of a transcutaneous energy transfer (TET) device for powering an artificial heart is shown in FIG. 2. FIG. 2 is a schematic drawing of EFS 100 embedded in a mattress 210. Also schematically shown is a human implant recipient 205 reclining on mattress 210. The implanted components include a total artificial heart 215, an internal battery 220, a secondary coil 230, internal electronics 240, and connecting wires 250. Embedded in the mattress are primary coils 110A and 110B (shown in an alternative, oval, configuration), controller 120, TET primary circuits 140, and power supply 130.

II. Primary Coils

As shown in FIG. 1, EFS 100 includes an exemplary configuration of two primary coils, primary coils 110A and 110B. It will be understood that many other configurations are possible in accordance with the present invention. Specifically, any number of primary coils may be included in other configurations. The primary coils are not limited to the square shape of coils 110 shown in FIG. 1 or the oval shape shown in FIG. 2. Coils 110 may be any shape in two or three dimensions, and the coils may be arranged in any pattern rather than be limited to the row pattern shown. The direction of current flow may be in the clockwise (CW) direction, rather than in the counter-clockwise (CCW) direction shown with respect to coils 110. Also, any number of loops may be included in each coil, for ease of illustration, one winding or loop is shown in the illustrative examples of coils 110.

As is well known to those skilled in the relevant art, the magnetic field (B) that is generated by a coil having "N" loops and a characteristic radius of "r" is given by equation $$B = \frac{\mu_o^{Ni}}{2r}, \quad (1)$$

in which $\mu_o$ is the permeability constant for free space (equal to $4\pi$ times $10^{-7}$ weber per ampere·meter), i is the current through the primary coil in amperes, r is expressed in meters, and B is therefore expressed in weber per square meter.

As also is well known, the magnetic field generated by a larger coil may be generated by a magnetically equivalent configuration of smaller coils. FIGS. 4A–4D provide illustrative examples. In FIG. 4A, currents in coils 410A–D (collectively referred to as coils 410) are shown as flowing in a clockwise direction. The coils 410 are roughly square shape, and are positioned at the corners of a square pattern. It will be understood that these current flows show an instantaneous or steady state direction, and that the direction may be reversed. It is assumed for illustrative purposes that, when a current flow is reversed, it is reversed for all energized primary coils in the same manner. Thus, for example, a comparison between two adjoining primary coils in which currents flow in opposite directions generally is applicable both to steady state and alternating current conditions. For clarity and convenience, references hereafter to the direction of current flow will be made with respect to an instantaneous or steady state direction. Alternatively, the direction of current flow may be considered to be the sense of direction of the winding of the coil.

As will be evident to those skilled in the relevant art, some components of the magnetic fields of coils 410 tend to cancel each other out. Specifically, those components generated by currents flowing in opposite directions, such as the loop-segment pairs 411 and 412, or 413 and 414, i.e., those in the interior of the square pattern, produce generally opposing magnetic fields. In contrast, magnetic fields generated by the loop-segments on the exterior of the square pattern, such as segments 415 and 416, are not opposed by magnetic fields generated by other loop segments in the pattern. Thus, the combination of magnetic fields generated by primary coils 410 is generally equivalent to the magnetic field generated by primary coil 420 of FIG. 4B.

Similarly, the combined magnetic field generated by primary coils 430A–H has a shape that is generally equivalent to the combined magnetic fields of primary coils 440. Specifically, the square pattern of coils 430A–D, having current flowing in a clockwise direction, produces a magnetic field generally equivalent to that produced by coil 440A, which also has clockwise current flow. The square pattern of coils 430E–H, having a counter-clockwise current flow, produces a magnetic field generally equivalent to that produced by coil 440B. Thus, the configuration of FIG. 4C is generally equivalent to that of FIG. 4D in terms of the magnetic fields produced by the coils of those figures.

Figure 5A:
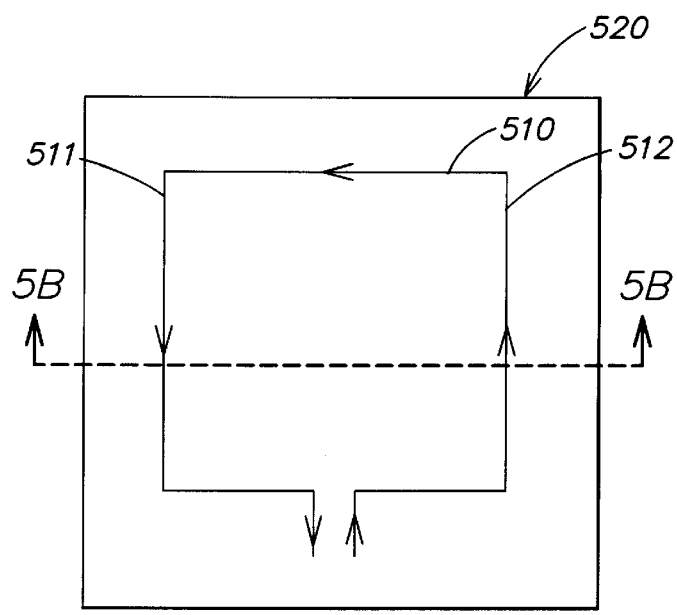
FIG. 5A is a schematic top plan view of a single primary coil such as may be employed in an exemplary embodiment of the electromagnetic field source of FIG. 1.
Figure 5B:
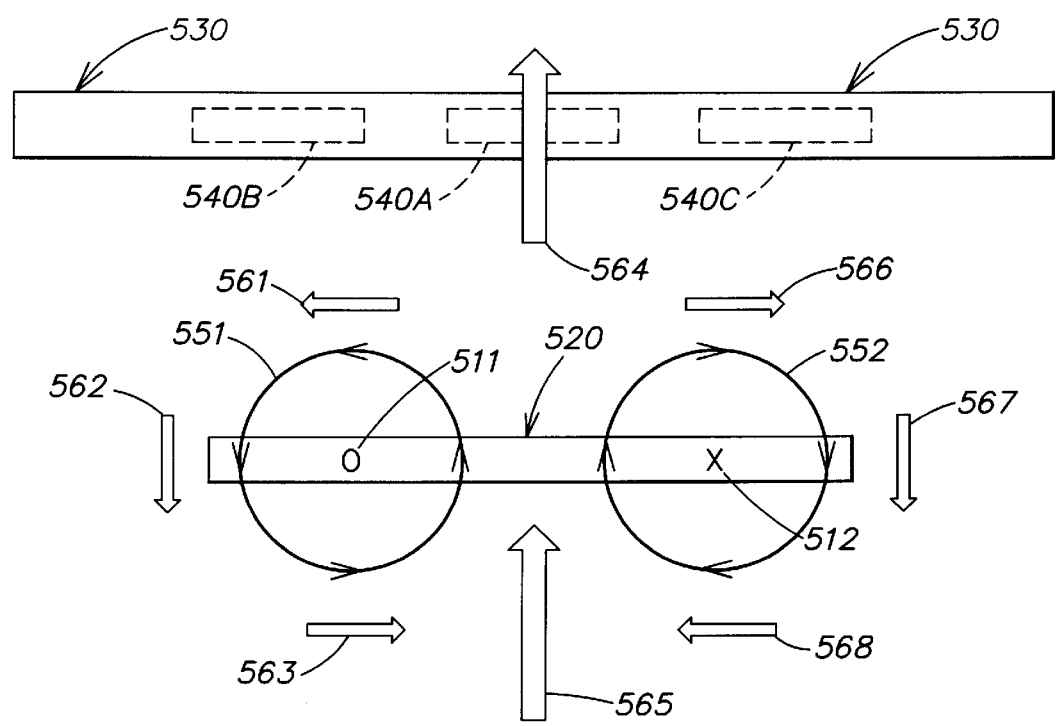
FIG. 5B is a schematic cross-sectional side view of the primary coil of FIG. 5A, showing magnetic fields produced by the primary coil.

FIGS. 5A and 5B provide greater detail with respect to the magnetic fields produced by a single primary coil such as coil 420 of FIG. 4B. FIG. 5A is a schematic top plan view of a single primary coil, coil 510, disposed in a plane 520. It will be assumed for illustrative purposes that plane 520 is horizontal. For example, it may be a plane in a horizontally disposed mattress, such as mattress 210. Current flows through coil 510 in a counter-clockwise direction. FIG. 5B is a cross-sectional side view along cross-section line 5B—5B through loop segments 511 and 512. The notations "O" and "X" in the cross section of plane 520 respectively represent current flow out of and into the drawing page through loop segments 511 and 512. Iso-magnetic contours 551 and 552 respectively represent the magnetic fields generated by current flowing through loop segments 511 and 512 in the described directions. The direction and magnitude of the magnetic fields are schematically represented by arrows 561–568. For illustrative purposes, relatively weak magnetic fields are represented by small arrows, and large arrows are used to represent stronger magnetic fields. It should be appreciated that such diagrammatic representations are representational only and are not intended to be precise with respect to their size, shape or orientation.

Also shown in FIG. 5B, but omitted from FIG. 5A for clarity, is a second horizontal plane 530 disposed above plane 520. It is assumed for illustrative purposes that a secondary coil 230 implanted in recipient 205 is disposed within plane 530 at a position represented in phantom outline by slot 540A. As shown, position 540A is located so that its projection on plane 520 is generally within the interior of coil 510.

Components of the magnetic fields generated by loop segments 511 and 512 generally reinforce each other in certain areas, such as the interior area of coil 510. These reinforced magnetic field components are represented by large arrows 564 and 565 that are directed upward from plane 520 toward plane 530. More specifically, magnetic fields represented by exemplary iso-magnetic contour lines 551 and 552 are oriented in the same direction (upward toward plane 530), and thus are reinforcing, in the regions of arrows 564 and 565. Elsewhere, such as in the regions of small arrows 561 and 566, there is no such reinforcement.

If secondary coil 230 is in position 540A, i.e., in a plane parallel to that of primary coil 510 and generally vertically aligned with the interior of coil 510, then, as is well known by those skilled in the relevant art, primary coil 510 induces a current to flow in secondary coil 230. The magnetic field that induces this current flow is represented by arrows 564 and 565. In contrast, if secondary coil 230 is disposed in plane 530 at a position generally outside of the interior of coil 510, such as positions 540B or 540C, then primary coil 510 generally does not induce a current to flow in secondary coil 230.

More specifically, the magnetic fields acting on secondary coil 230 when in position 540B or 540C generally are in the same or parallel plane as the coils, and thus, as is well known, induce weak or no current with the coils. In addition, even if secondary coil 230 were perpendicular to the direction of the magnetic field, those fields outside the perimeter of the primary coil (such as are represented by arrows 561 or 566) generally are weaker than those in the interior (such as represented by arrow 564). For convenience, such areas in the magnetic fields; i.e., those that induce weak or no currents in secondary coils located in those areas, are referred to hereafter as "dead zones."

Figure 6A:
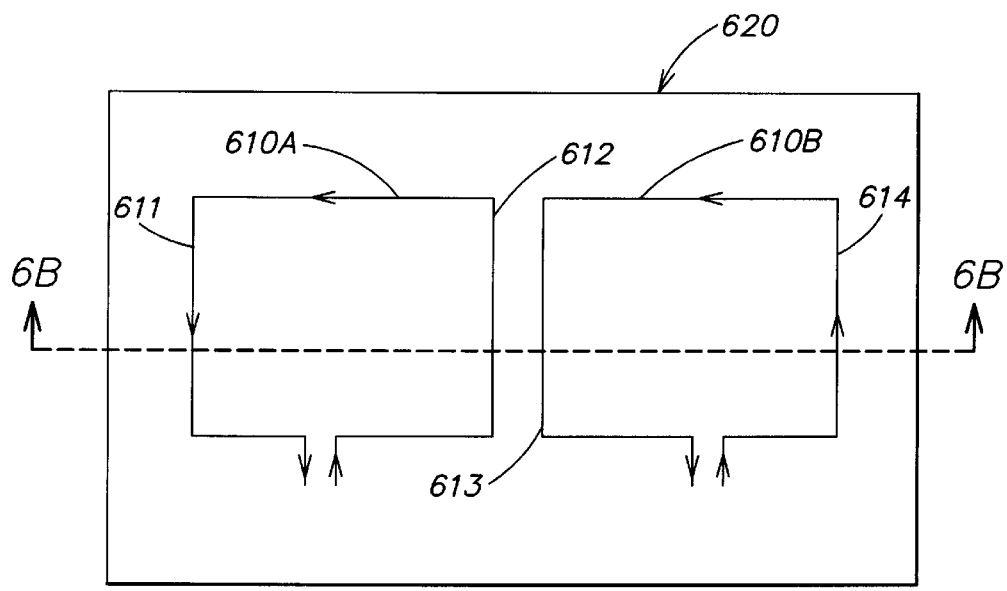
FIG. 6A is a schematic top plan view of two adjacent primary coils, having current flows in the same direction, such as may be employed in an exemplary embodiment of the electromagnetic field source of FIG. 1.
Figure 6B:
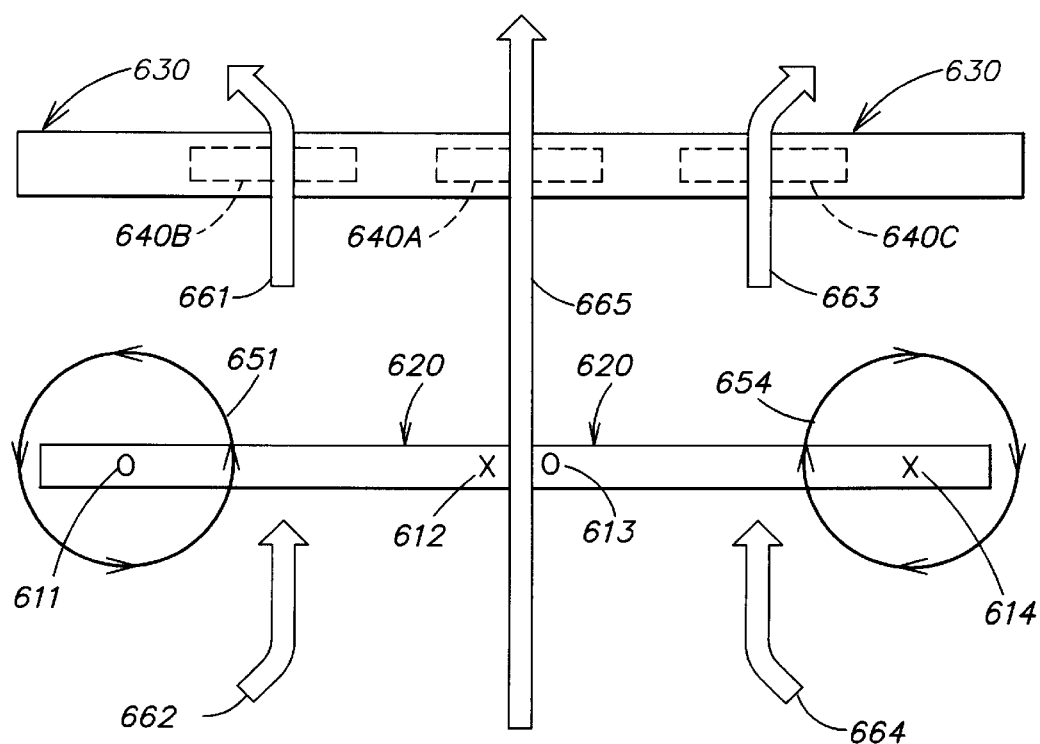
FIG. 6B is a schematic cross-sectional side view of the primary coils of FIG. 6A, showing magnetic fields produced by the primary coils.

FIGS. 6A and 6B provide greater detail with respect to the magnetic fields produced by two primary coils in proximity to each other, such as coils 110 shown in FIG. 1. FIG. 6A is a schematic top plan view of primary coils 610A and 610B (coils 610), disposed in a horizontal plane 620. Current flows through both of coils 610 in the same direction, i.e., counter-clockwise in this example. FIG. 6B is a cross-sectional side view of coils 610 in FIG. 6A taken along cross-section line 6B—6B. Iso-magnetic contours 651–654 respectively represent the magnetic fields generated by current flowing through loop segments 611–614 in the indicated directions.

As noted, the magnetic fields in the interior of the coils tend to reinforce, and thus produce combined magnetic fields such as are represented by large arrows 661 and 662 (with respect to coil 610A) and 663 and 664 (with respect to coil 610B). Also, between coils 610A and 610B the magnetic fields generated by loop segments 612 and 613 tend to reinforce each other in the upward direction, as represented by large arrow 665.

A second horizontal plane 630 is shown above plane 620 in FIG. 6B, but is omitted from FIG. 6A for clarity. As with respect to FIG. 5B, it is assumed for illustrative purposes in FIG. 6B that secondary coil 230 may be positioned in various locations in plane 630, as indicated by representative regions 640A–640C shown in phantom outline. A horizontally-disposed secondary coil 230 is activated when located in any region 640 due to then orthogonal intersection with the vertically-oriented magnetic fields generated by primary coils. The word "activated" means in this context that one or more primary coils have produced a magnetic field of any strength, and in an orientation, sufficient to induce an operative current in secondary coil 230. The word "operative" means that the current is sufficient to enable secondary coil 230 to perform its finction, such as powering circuits related to artificial heart 215 or recharging internal battery 220.

Figure 7A:
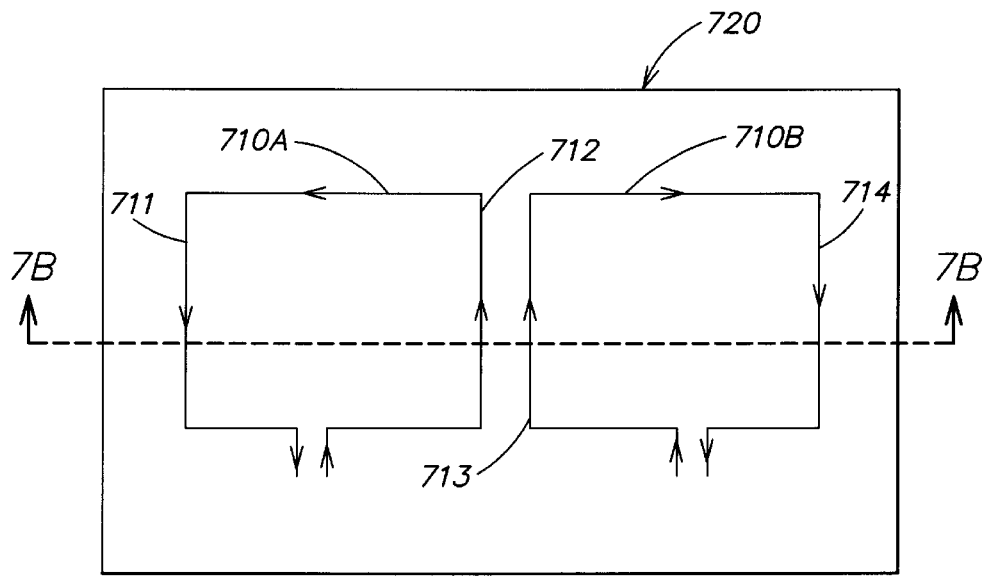
FIG. 7A is a schematic top plan view of two adjacent primary coils, having current flows in opposite directions, such as may be employed in an exemplary embodiment of the electromagnetic field source of FIG. 1.
Figure 7B:
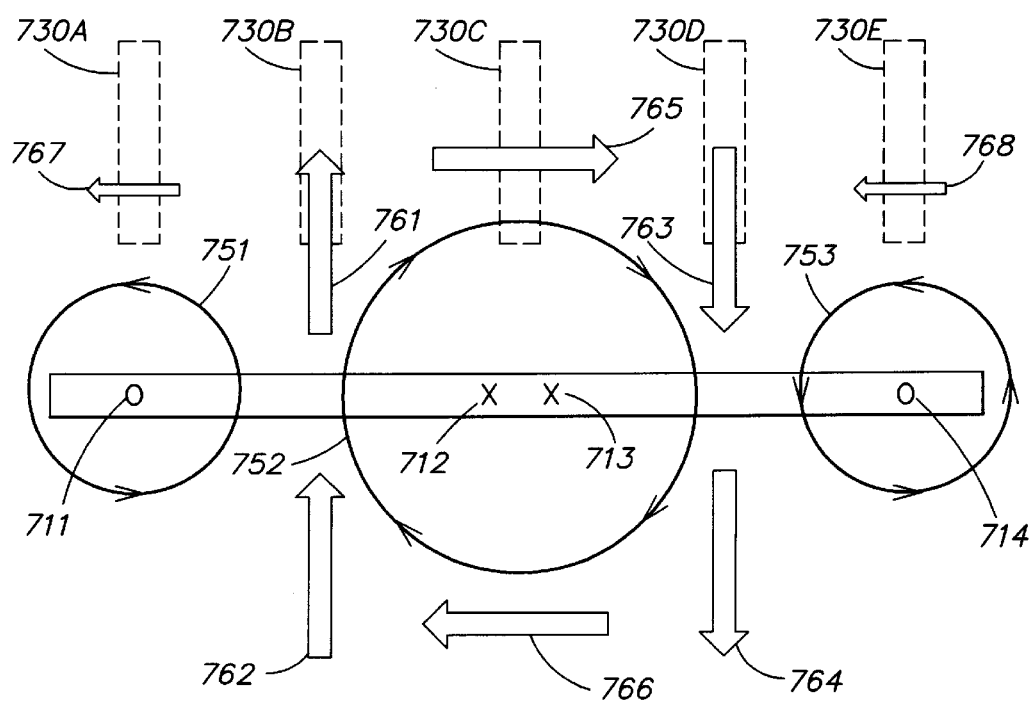
FIG. 7B is a schematic cross-sectional side view of the primary coils of FIG. 7A, showing magnetic fields produced by the primary coils.

Another case is now considered in which current is flowing in opposite directions through two adjacent primary coils. FIG. 7A is a schematic top plan view of primary coils 710A and 710B (coils 710), disposed in a horizontal plane 720. Current flows through coil 710A in a counter-clockwise direction, and current flows through coil 710B in a clockwise direction. FIG. 7B is a cross-sectional side view taken along cross-section line 7B—7B through loop segments 711 and 712 of coil 710A and loop segments 713 and 714 of coil 710B. Current flows out of the drawing page through loop segments 711 and 714, and into the drawing page through loop segments 712 and 713. Iso-magnetic contours 751 and 753 respectively represent the magnetic fields generated by current flowing through loop segments 711 and 714. Iso-magnetic contour 752 represents the combined magnetic field generated by current flowing through loop segments 712 and 713.

Large arrows 761 and 762 represent the relatively strong magnetic fields generated in a vertical direction in the interior of primary coil 710A due to reinforcement, as described above. Similarly, large arrows 763 and 764 represent the relatively strong magnetic fields generated in a vertical direction in the interior of primary coil 710B. In contrast, in accordance with effects well known by those skilled in the relevant art, the magnetic fields generated by loop segments 712 and 713 tend to generate a relatively strong magnetic field in a horizontal direction. This horizontal magnetic field between coils 710A and 710B is represented by large arrows 765 and 766. Also, non-reinforced magnetic fields are generated in a generally horizontal orientation by loop segments 711 and 714, as indicated by small arrows 767 and 768.

A representative series of five vertical positional slots 730A–E (positions 730) are shown above plane 710 in FIG. 7B, but are omitted from FIG. 7A for clarity. It is assumed for illustrative purposes that secondary coil 230 may be positioned in any position 730 or therebetween. If secondary coil 230 is positioned in positions 730B or 730D, i.e., vertically oriented approximately over the middle of coils 710A and 710B, respectively, coil 230 generally will not be activated. Lack of activation is due to the fact that the vertical orientation of secondary coil 230 coincides with the vertical orientations of the magnetic fields (arrows 761 and 763) in these locations. If secondary coil 230 is positioned in position 730C approximately between coils 710A and 710B, it generally is activated because the vertical orientation of secondary coil 230 is perpendicular to the horizontal orientation of the magnetic field (arrow 765) at this location.

Similarly, secondary coil 230 generally is activated if it is positioned in positions 730A or 730E, that is, approximately over the exterior loop segments 711 and 714 of coils 710A and 710B, respectively. The word "exterior" is used in this context to refer to loop segments of an energized primary coil located generally opposite to loop segments of the same coil that are close to loop segments of another energized primary coil. Activation is attained because the vertical orientation of secondary coil 230 is perpendicular to the horizontal magnetic field.

However, because the magnetic fields represented by arrows 767 and 768 are not reinforced, it may be necessary to increase the strength of these fields in order to sufficiently activate secondary coil 230 to meet desired performance standards. As indicated by equation number one, one way to increase the magnetic fields represented by arrows 767 or 768 is to increase the current through primary coils 710A or 710B, respectively. For example, if coils 710 are located at the edge, then the currents may be increased. Also, the number of loops in the primary coils may be increased based on a determination of the strength that these weaker magnetic fields must exhibit in order to activate secondary coil 230.

Aspects of the operation and arrangement of primary coils of EFS 100 are now further described with respect to an illustrative example. It is assumed in this example that recipient 205 may move to any position on mattress 210, and assume any orientation between horizontal (i.e. lying on the back or stomach) and vertical (i.e., lying on a side). Also, recipient 205 may be positioned immediately above mattress 210, or at a greater distance from it, as when lying on pillows or sitting in bed. Thus, secondary coil 230 may be aligned above any portion of mattress 210, may be located either on or at a distance from mattress 210, and may be disposed in any orientation with respect to the plane of mattress 210.

In accordance with one embodiment, a small number of relatively large primary coils, such as coils 110A and 110B as shown in FIG. 2, may be used. FIGS. 8A–8D show three illustrative configurations employing a small number of large primary coils in a horizontally disposed mattress 800.

Figure 8A:
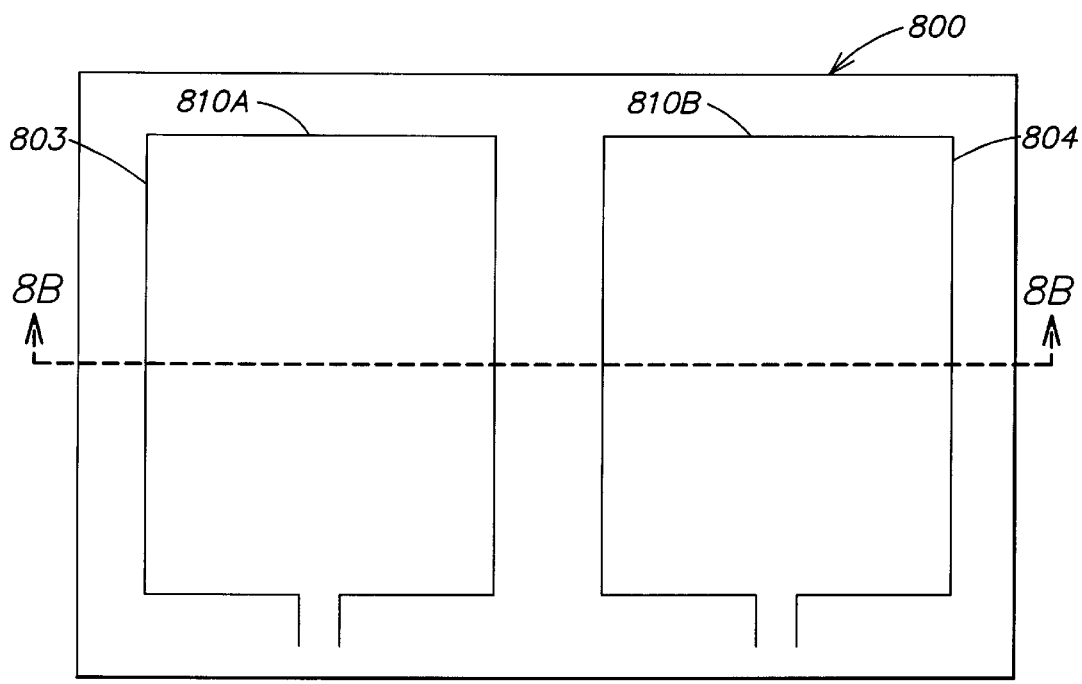
FIG. 8A is a schematic cross-sectional top view of two horizontally disposed primary coils in the same plane such as may be employed in an exemplary embodiment of the electromagnetic field source of FIG. 1, including a mattress in which the coils are embedded.
Figure 8B:
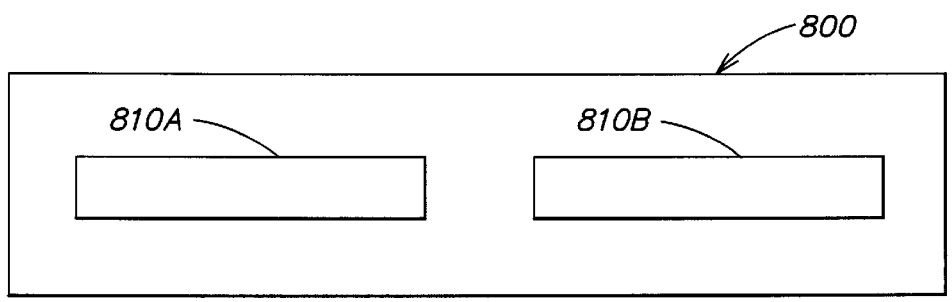
FIG. 8B is a schematic cross-sectional side view of the primary coils and mattress of FIG. 8A.

FIG. 8A is a schematic cross-sectional top view of mattress 800 including primary coils 810A and 810B (coils 810). FIG. 8B is a cross-sectional side view of the configuration of FIG. 8A along cross-section line 8B—8B. The configuration of FIGS. 8A and 8B is similar to that of FIG. 1 with respect to the location of primary coils 110. As shown in FIG. 8B, coils 810 are disposed approximately in the same plane.

It may first be assumed that secondary coil 230 is positioned above either primary coil 810A or 810B (i.e., so that the vertical projection of secondary coil 230 falls approximately within one of coils 810). It is also assumed that secondary coil 230 is horizontally disposed; i.e., it is in approximately the same plane as primary coils 810. In this case, secondary coil 230 may be activated by providing current, in either direction, to whichever of coils 810 secondary coil 230 is above. This primary coil is referred to for convenience as the "closest" primary coil, meaning that it is the "closest" of the primary coils to the secondary coil. Hereafter, "closest" similarly will be used to mean the primary coil, or group of primary coils, that are closer to the secondary coil than any other primary coils.

The closeness, or proximity, of coils to each other may be defined and determined in different ways, depending, for example, on the type of proximity sensor that is used. Thus, for a resonance frequency shift sensor, such as is described below with respect to the operations of proximity detector 126, closeness generally relates to magnetic proximity in the sense that coils are closest if their mutual inductance is strongest. If other kinds of sensors are used, such as optical or mechanical sensors, closeness generally relates to the physical proximity of the coils.

It is now assumed for illustrative purposes that secondary coil 230 is positioned above and approximately between coils 810. In this case, secondary coil 230 may be activated by applying currents to coils 810A and 810B in the same direction. The magnetic fields generated by coils 810 thus generally are as shown in FIG. 6B with respect to coils 610. That is, a strong, vertically oriented, magnetic field (such as shown by arrow 665 of FIG. 6) perpendicularly intersects horizontally positioned secondary coil 230.

Secondary coil 230 is now assumed to be disposed in a vertical orientation and located approximately between primary coils 810. In this case, secondary coil 230 may be activated by applying currents to coils 810A and 810B in opposite directions. The magnetic fields generated by coils 810 thus generally are as shown in FIG. 7B with respect to coils 710. That is, a strong, horizontally oriented, magnetic field (such as shown by arrow 765 of FIG. 7) perpendicularly intersects vertically positioned secondary coil 230. Similarly, if secondary coil 230 is positioned generally above an exterior loop segment of coils 810, such as loop segments 801 or 802, it will be intersected by a magnetic field perpendicular to it, although this field generally will be weaker than the one between the coils. However, as noted above with respect to similar fields 767 and 768 of FIG. 7, secondary coil 230 may be activated by increasing the current through the closest coil so that the magnetic field is increased in strength, or by varying other parameters such as the number of loops in the primary coils.

Finally, the case is considered in which secondary coil 230 is disposed in a vertical orientation and located approximately above the middle of one of primary coils 810. In this case, it generally is not possible to activate secondary coil 230 because it is in approximately the same plane as the magnetic field generated by the closest primary coil. This situation is shown in FIGS. 6B and 7B with respect to vertically oriented magnetic field arrows 661, 663, 761, and 763. Thus, the configuration of FIG. 8B; i.e., in which the primary coils are in the same horizontal plane, generally is not appropriate if secondary coil 230 may be in a predominantly vertical orientation and it is required that it may be activated at every location over horizontal mattress 800.

However, the configuration of FIG. 8B may nonetheless be employed in a variety of circumstances. For example, secondary coil 230 may be constrained to remain predominantly in a horizontal position, i.e., in a plane predominantly parallel to the plane of the primary coils. Alternatively, more than one secondary coil may be used; for example, two secondary coils that are perpendicularly oriented with respect to each other may be employed.

To illustrate a more general case, it is now assumed that the primary coils of EFS 100 must be positioned so that one or more of them may activate a single secondary coil 230 irrespective of the location or orientation of recipient 205 with respect to mattress 210. For convenience, this illustrative condition is referred to as a requirement for "full coverage." It will be understood that, in alternative embodiments, full coverage need not be required. For example, in some applications it may be provided that a secondary coil need not be activated if it is located at certain positions on or over the housing of the primary coils, or, as just noted, is disposed in particular orientations.

Figure 8C:
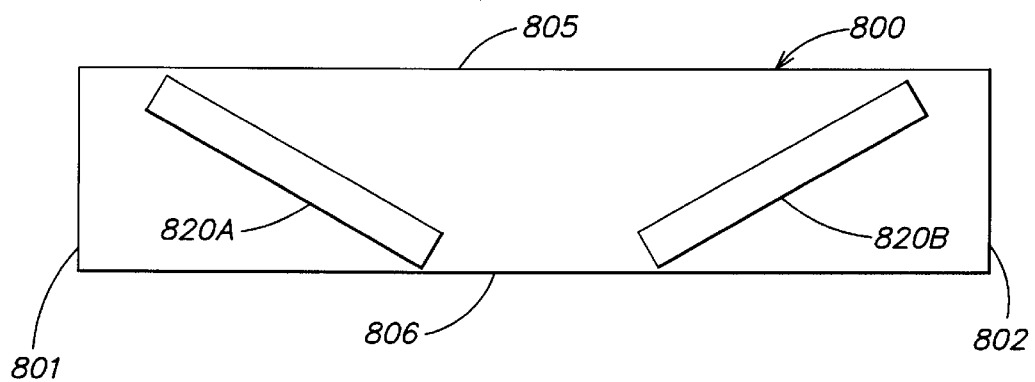
FIG. 8C is a schematic cross-sectional side view of two primary coils disposed at opposing acute angles to the horizontal, such as may be employed in an exemplary embodiment of the electromagnetic field source of FIG. 1, including a mattress in which the coils are embedded.

FIGS. 8C, 8D, 9A, and 9B show illustrative configurations that may be used to achieve full coverage. It will be understood that many alternative configurations are possible. In FIGS. 8C, 8D, 9A, and 9B, in contrast with the configuration of FIGS. 8A and 8B, the primary coils of EFS 100 are not disposed in the same plane. FIG. 8C is an illustrative example of two primary coils 820A and 820B (coils 820) that are similar to primary coils 810 except that they are disposed on separate, intersecting, planes. In particular, coil 820A forms an acute angle from near the center of the bottom surface 806 of mattress 800 upwards towards side 801 and top surface 805 of mattress 800. Primary coil 820B similarly forms an acute angle from near the center of the bottom surface 806 upwards towards an opposite side 802 of mattress 800. Thus, primary coils 820 form a roughly "V" shape in cross section.

Assuming again for convenience of reference that mattress 800 is horizontally oriented, both of coils 820 may generate magnetic fields that are perpendicular to their planes and thus have both horizontal and vertical components. Therefore, if secondary coil 230 is vertically disposed at any point above the interiors of either of coils 820, a horizontal component of the magnetic field of the closest of primary coils 820 may be generated in order to activate secondary coil 230. As is evident, the amount of current required to activate secondary coil 230 depends, among other things, on the angles of coils 820 with respect to the horizontal, and on the sizes and numbers of loops of the coils. Also because of the presence of both horizontal and vertical components, and for the reasons discussed above with respect to inter-coil magnetic fields as illustrated in FIGS. 6B, 7B, and 8B, a vertically oriented secondary coil 230 also is activated if it is located between coils 820.

Similarly, because coils 820 generate magnetic fields having vertical components, secondary coil 230 is activated if it is located anywhere over the surface of mattress 800 and oriented horizontally. This case is similar to that of FIG. 8B except that, other factors being equal, the magnitudes of the vertical magnetic field components of coils 820 generally will be less than those of coils 810 because of the angular orientations of coils 820 with respect to the horizontal.

Figure 8D:
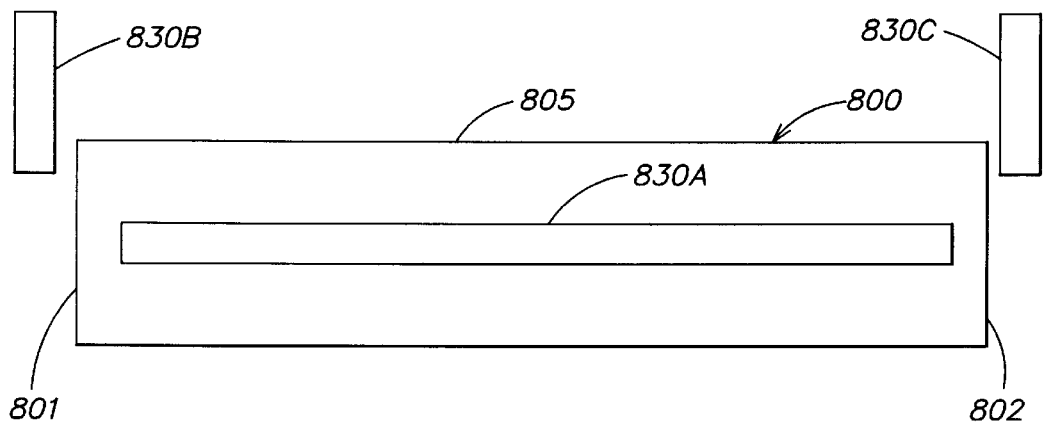
FIG. 8D is a schematic cross-sectional side view of one horizontally disposed primary coil and two vertically disposed primary coils at opposing ends of the horizontal coil, such as may be employed in an exemplary embodiment of the electromagnetic field source of FIG. 1, including a mattress in which the coils are embedded.

FIG. 8D illustrates an alternative configuration in which horizontal primary coil 830A is positioned between two vertical primary coils 830B and 830C. In this exemplary configuration, coil 830A is embedded in mattress 800 whereas coils 830B and 830C adjoin opposing sides 801 and 802 of mattress 800, respectively. Coils 830B and 830B may be contained within side boards of a bed including mattress 800, for example. Primary coil 830A thus is capable of generating vertically oriented magnetic fields, and primary coils 830B and 830C are capable of generating horizontally oriented magnetic fields, across all of top surface 805. Secondary coil 230 thus may be activated irrespective of its position or orientation above mattress 800, provided that it is not too far removed from mattress 800. As is evident, the operational range of secondary coil 230 above top surface 805 depends on the strength of the magnetic fields generated by primary coils 830 and by the height above top surface 805 of primary coils 830B and 830C.

It will be understood, based on the description above with respect to FIGS. 4A–4D, that any of the primary coils represented in FIGS. 8A–8D may be replaced with magnetically equivalent groups of smaller primary coils. For example, primary coil 830A may have a perimeter that is approximately co-extensive with the perimeter of top surface 805 of mattress 800. It may be replaced with a functionally equivalent array of smaller primary coils arranged so that the exterior loop segments of the array also are generally co-extensive with the perimeter of top surface 805. Thus, in one of many possible configurations, primary coil 830A may have a shape similar to that of primary coil 420 of FIG. 4B, and it may be functionally replaced with an array of four smaller or eight even smaller primary coils arranged and configured as shown in FIG. 4A with respect to primary coils 410.

Figure 9A:
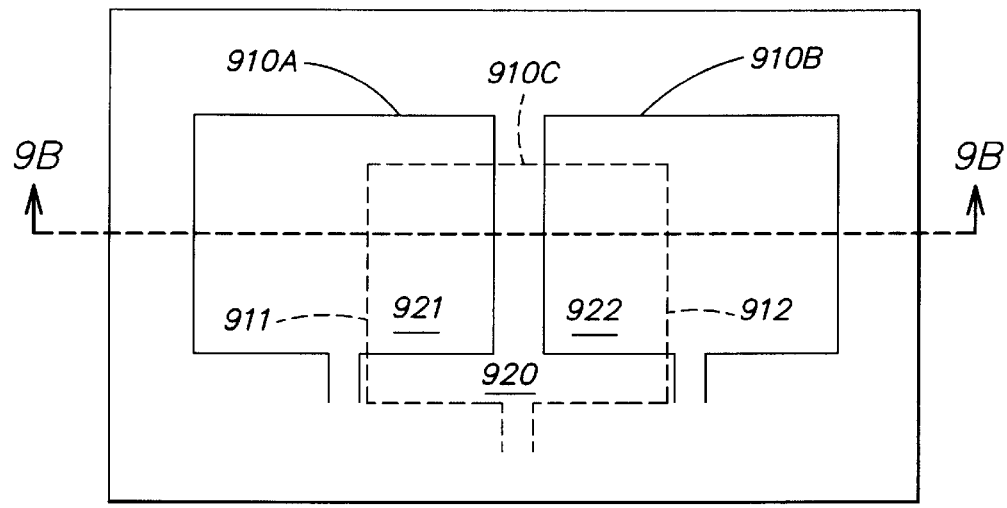
FIG. 9A is a schematic cross-sectional top view of three horizontally disposed primary coils, two of which are in the same plane and the third of which is in a parallel plane, such as may be employed in an exemplary embodiment of the electromagnetic field source of FIG. 1, including a mattress in which the coils are embedded.
Figure 9B:
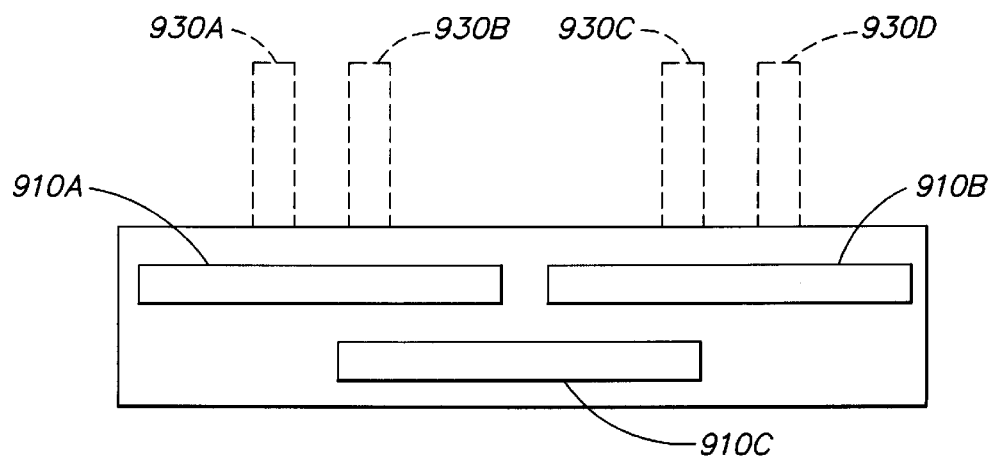
FIG. 9B is a schematic cross-sectional side view of the primary coils and mattress of FIG. 9A.

Yet another type of configuration that may be used to achieve full coverage is shown illustratively in FIGS. 9A and 9B. FIG. 9A is a schematic cross-sectional top view of three horizontally disposed primary coils 910A–C (coils 910). FIG. 9B is a schematic cross-sectional side view of coils 910 along cross-section line 9B—9B. Two of the coils, 910A and 910B, are in approximately the same plane, as indicated in FIG. 9B. The third coil, 910C, is in a plane that is approximately parallel to, and below (or, in an alternative implementation, above), the plane of coils 910A and 910B. As seen from the top-view perspective of FIG. 9A, an overlap area 921 is defined by the vertical projection of coil 910C on coil 910A, and a similar overlap area 922 is defined by the vertical projection of coil 910C on coil 910B. Also, an inter-coil area 920 is shown that is between coils 910A and 910B, but within the projection of coil 910C.

As noted with respect to FIG. 6B, a horizontally disposed secondary coil 230 positioned between two first primary coils in the same plane may be activated by energizing both first primary coils using current flowing in the same direction. Alternatively, such a disposed secondary coil may be activated by energizing another primary coil that is positioned between the first primary coils in another plane. For example, if secondary coil 230 is located in inter-coil area 920 between coils 910A and 910B, it may be activated either by energizing coils 910A and 910B with current flowing in the same direction, or by energizing coil 910C. Because secondary coil 230 is, in this example, positioned above the interior of coil 910C, it will be activated by a vertical magnetic field generated by coil 910C above its interior.

Importantly, the configuration of FIGS. 9A and 9B may also be used to achieve full coverage with respect to secondary coil 230 in a vertical orientation. As noted, a vertically disposed secondary coil 230 generally positioned between two primary coils, or above exterior loop segments, may be activated by energizing both primary coils using current flowing in opposite directions. However, as also noted, vertically oriented secondary coil 230 positioned above the middle of a primary coil generally may not be activated by that coil. Nonetheless, such a positioned and oriented secondary coil may be activated by a primary coil generally positioned so that one of its exterior loop segments is aligned with the middle of the other primary coil. For example, primary coil 910C, having exterior loop segments 911 and 912, may activate secondary coil 230 if it is vertically oriented and positioned in positions 930B or 930C, respectively. These positions are generally aligned with exterior loop segments 911 and 912, and thus a weaker, horizontally oriented, magnetic field is produced through those positions in the manner shown by arrows 767 and 768. As is evident, the magnitude of this magnetic field generally decreases with distance from the energized loop segment; thus, the magnetic field at regions/positions 930A or 930D generally will be weaker than those at 930B or 930C. In addition to the previously noted steps of increasing current or number of loops, this potential deficiency in full coverage may be avoided by providing interlaced arrays of primary coils in two or more planes.

Figure 10:
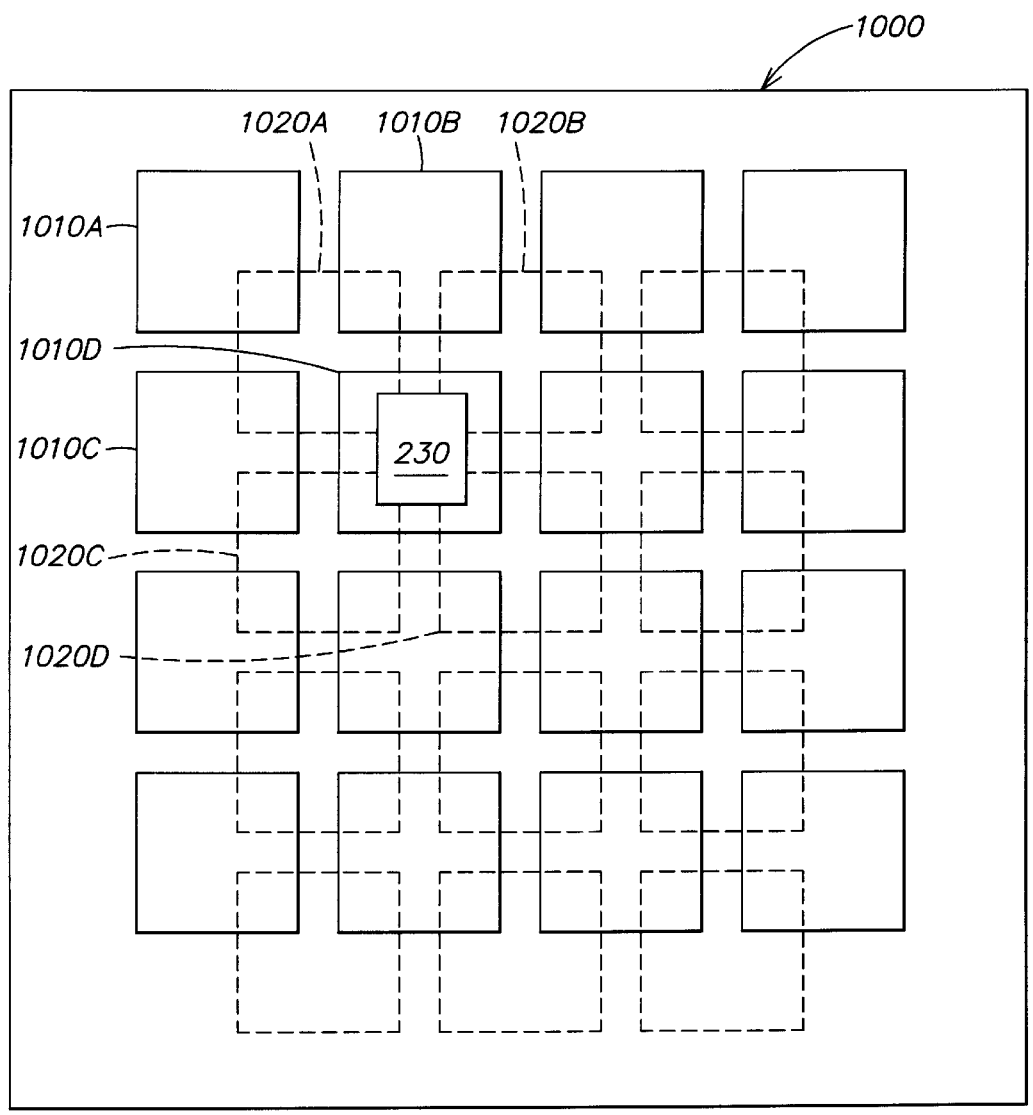
FIG. 10 is a schematic cross-sectional top view of a two-plane, interlaced, array of horizontally disposed primary coils such as may be employed in an exemplary embodiment of the electromagnetic field source of FIG. 1, including a mattress in which the coils are embedded.

FIG. 10 illustrates one example of interlaced arrays of primary coils. In addition to addressing potential deficiencies in full coverage, such arrays may have an additional benefit of reducing the amount of power required by EFS 100. That is, less power generally is required to activate a secondary coil by generating a magnetic field from a small primary coil close to the secondary coil than from a more distant primary coil or from a large primary coil covering a large area. Arrays of smaller primary coils provide that one or more of the primary coils will be close to the secondary coil, and thus less power generally will be required than if more distant, or larger, primary coils were employed. In some applications, a similar benefit is derived from the fact that the magnetic field generated by a small primary coil of an array is more localized than the magnetic field generated by a large primary coil. For example, the generation of large-area magnetic fields may interfere with medical equipment, or adversely interact with metallic objects in or around the recipient.

It will be understood that although the configurations of FIGS. 9A, 9B, and 10 are described herein for convenience as having primary coils disposed in two planes (which may include additional planes in alternative configurations), the coils in those planes may, in practice, be very close together. They may be so close as to essentially provide a single plane with interwoven primary coils. For example, FIG. 10 is a schematic cross-sectional top view that shows what is referred to as two parallel planes of primary coils. A first plane, shown in solid lines, includes representative coils 1010A–D of an array of first-plane primary coils 1010. A second plane, referred to as including an array of second-plane primary coils, is shown in phantom outline. Coils 1020A–D are representative of this array of second-plane primary coils 1020. In one of many possible implementations, coils 1010 and 1020 may consist of wires woven into, or positioned within, a blanket such that the loop segments of coils 1010 cross under, and may touch (if electrically insulated), loop segments of coils 1020 where they cross. For clarity and convenience of illustration, coils 1010 and 1020 are schematically represented by squares that are disposed within a horizontally oriented mattress 1000. Lead wires into and out of the coils are not shown for clarity.

As is evident from FIG. 10 and the preceding description relating to FIGS. 9A and 9B, coils 1010 and 1020 provide full coverage over the surface of mattress 1000. (As also is evident, coverage at the perimeter of mattress 1000 may be achieved by the placement of primary coils adjacent to this perimeter, which are also omitted in FIG. 10 for clarity.) Full coverage using two planes of primary coils has already been described with respect to FIGS. 9A and 9B. In that description, however, it was noted that a vertically oriented secondary coil 230 positioned as in positions 930A or 930D, i.e., at some distance from the external loop segment of the closest primary coil, may not be activated unless current is increased, or another measure is taken, to increase the magnetic field generated by that external loop segment. The arrays of primary coils 1010 and 1020 provide an alternative way of providing that secondary coil 230, in such orientation and position, will be activated.

For example, it is assumed that secondary coil 230 is vertically oriented and positioned in the middle of first-plane primary coil 1010D, as schematically represented in FIG. 10. Secondary coil 230 may be activated by energizing any one, or any combination, of second-plane primary coils 1020A–D. Similarly, if secondary coil 230 is vertically oriented and positioned approximately in the middle of second-plane primary coil 1020A, it may be activated by energizing any one, or any combination, of first-plane primary coils 1010A–D. It should be understood that primary coils 1010A–D may be at other orientations, such as at a 45° orientation. As is evident from FIG. 10, the size of primary coils 1010 and 1020 generally may be determined by the size of secondary coil 230, among other factors.

Alternative, but not exhaustive, ways of providing full coverage have now been described. These alternatives depend on various configurations of primary coils, the selection of one or more primary coils closest to the secondary coil, the orientation of the secondary coil with respect to the plane or planes of the primary coils, and the strength of the magnetic fields based on various factors such as current strength and the direction of the magnetic field by proper choice of current directions through the coils. Now to be described are the operations of EFS 100 with respect to determining which of the primary coils are closest, the orientation of the secondary coil, and the amount of current to provide to the closest primary coils.

III. Controller

As noted, controller 120 selectively provides current to one or more primary coils based on their proximity, and/or orientation with respect, to the secondary coil. For convenience, controller 120 is hereafter equivalently described as selectively providing current to one or more primary coils based on their "position" with respect to the secondary coil. As shown in FIG. 1, controller 120 includes current director 124, proximity detector 126, and orientation detector 122, the operations of which are now described.

A. Current Director

Current director 124 selectively directs time-varying currents through the closest primary coils. Current director 124 operates in cooperation with TET primary circuits 140 and power supply 130. Specifically, TET primary circuits 140, powered by power supply 130, fashion alternating currents suitable for energizing primary coils in a TET. TET primary circuits 140 may include any of a variety of known circuits for performing such a function, or may include circuits to be developed in the future. The functions of current director 124 are shown in greater detail in FIG. 3.

1. Power Adjuster

Current director 124 includes power adjuster 310 that adjusts the amount of current directed to the closest primary coils based on a number of factors. Any of a variety of known techniques may be used to effectuate such adjustment; for example, any known amplifier circuit may be employed.

One factor in determining the amount of adjustment is the proximity of the secondary coil to the closest primary coils. In one exemplary embodiment, a default value for the amount of current may be assumed by power adjuster 310. This default value may, for example, be a minimum value that will activate secondary coil 230 if it is located at a distance from the plane of the primary coils within an average range. This value may be determined empirically, by computation, or by a combination thereof. It is assumed for illustrative purposes that the anterior-posterior dimension of an average person ranges from nine to twelve inches in the area of the abdomen where a secondary coil may be implanted for operating a total artificial heart. If the primary coils are implanted two inches below the top surface of a mattress on which the recipient reclines, the default value may be such that secondary coil 230 will be activated if it is located 14 inches from the closest primary coils. If proximity detector 126 detects that secondary coil 230 may be further from the closest primary coils than 14 inches in this illustrative example, power adjuster 310 may increase the amount of current so that the magnetic fields generated by the closest primary coils nonetheless will be sufficient to activate secondary coil 230.

The amount of current required to activate secondary coil 230 also depends, as noted, on the size, shape, and number of loops of the closest primary coils. In the illustrated embodiment, the number of loops in each primary coil is predetermined in accordance with calculations based on equation number one, above, using an assumed size of secondary coil 230. As will be evident to those skilled in the relevant art, many other known equations and techniques may be used to determine a default, or other, current value.

To provide one example with respect to the illustrated embodiment, it is assumed that secondary coil 230 is circular with a diameter of three inches. It may be determined empirically, in view of the requirements of a typical total artificial heart 215 and battery 220, that the required magnetic field for effective coupling to this secondary coil 230 is approximately $10^{-4}$ weber/meter$^2$. To generate $10^{-4}$ weber/meter$^2$, a combination of N=3 turns, i=4 amperes, and r=0.05 meter (4" diameter) is adequate in typical circumstances in which secondary coil 230 is closely coupled to the closest primary coil. Assuming that secondary coil 230 may be on the order of 12 inches away from secondary coil 230, the number of primary turns may be increased to maintain the same field strength without an increase in the current used. A combination of N=9 turns, i=4 amperes, and r=0.15 meter (12" diameter or square edge) is typically adequate to activate secondary coil 230 under these assumed circumstances. It will be understood that these calculations are illustrative only, and that many other solutions are possible under alternative assumptions.

As noted, the orientation of secondary coil 230 may indicate that the current to the closest primary coils should be increased (or, alternatively, that the number of loops in each primary coil be increased to take orientation into account). For example, if secondary coil 230 is determined to be predominantly perpendicular to the plane or planes of the primary coils, and located above an external loop segment of the closest primary coil (e.g. position 730A of FIG. 7) rather than between closest primary coils (e.g. position 730C), then power adjuster 310 may increase current in order to increase the strength of the magnetic field generated by the closest primary coil.

Further, as noted, a typical distance from implanted secondary coil 230 to the surface of a mattress may be greater for a recipient lying on his or her side than if the recipient were in lying on his or her stomach or back. Also, the recipient may not be lying directly on the mattress, but may be reclining on pillows, sitting up, or be otherwise disposed away from the mattress. In the illustrated embodiment, proximity detector 126 detects such greater-than-normal distance, and power adjuster 310 therefore increases the amount of current. In other embodiments, a worst-case situation may be assumed such that it is not necessary to adjust the amount of current to the closest primary coils. That is, the default value is great enough to ensure that secondary coil 230 will be activated within any foreseeable range of distances from the primary coils. In such embodiments, power adjuster 310 need not be included.

2. Current Direction Determiner

Current director 124 also includes current direction determiner 320 that determines the directions of current supplied to two or more closest primary coils. In some instances, there may be only one closest primary coil, in which case current direction determiner 320 need not be employed. For example, secondary coil 230 may be positioned above the middle of a primary coil and oriented in the same plane as that coil (e.g., it is positioned in position 640B of FIG. 6). Thus, only that primary coil need be energized and direction of current flow is immaterial with respect to alternating current through a single coil. In other instances, however, it may be required to energize two or more primary coils.

For example, secondary coil 230 may be positioned between two closest primary coils in approximately the same plane as those coils (e.g, it is positioned in position 640A of FIG. 6). To activate secondary coil 230 in this position, the two closest primary coils are energized, with current flowing in the same direction (in phase). In another illustrative example, secondary coil 230 may be approximately above the middle of the square pattern made by primary coils 410 of FIG. 4A; that is, at location 418 between these four coils. If all four of coils 410 are energized by current flowing in the same direction, then, as noted, coils 410 are magnetically approximately equivalent to coil 420 of FIG. 4B. Thus, secondary coil 230 is activated by the energizing of coils 410 because such energizing is the approximate equivalent of energizing a coil having a center below, and in the same plane as, the secondary coil.

Current direction determiner 320 thus analyzes information from proximity detector 126 and orientation detector 122 to determine the relative directions of current flow in the two or more closest primary coils. Such analysis may be carried out in accordance with any of a variety of known techniques. For example, firmware including analog-to-digital converters and logical elements may be employed; appropriate software may be executed by a microprocessor (not shown); analog electrical comparator circuits may be employed, and so on.

3. Primary Coil Selector

Also included in current director 124 is primary coil selector 330 that selects primary coils to receive current. In the illustrated embodiment, this selection is made based on information provided by proximity detector 126 and orientation detector 122, as described below. Specifically, one or more primary coils are selected based on the detected location and orientation of secondary coil 230 and in accordance with the characteristics of magnetic fields described above. Typically, such selection is made in cooperation with the determinations made by current direction determiner 320, and in accordance with known techniques as noted with respect to current direction determiner 320.

Figure 3:
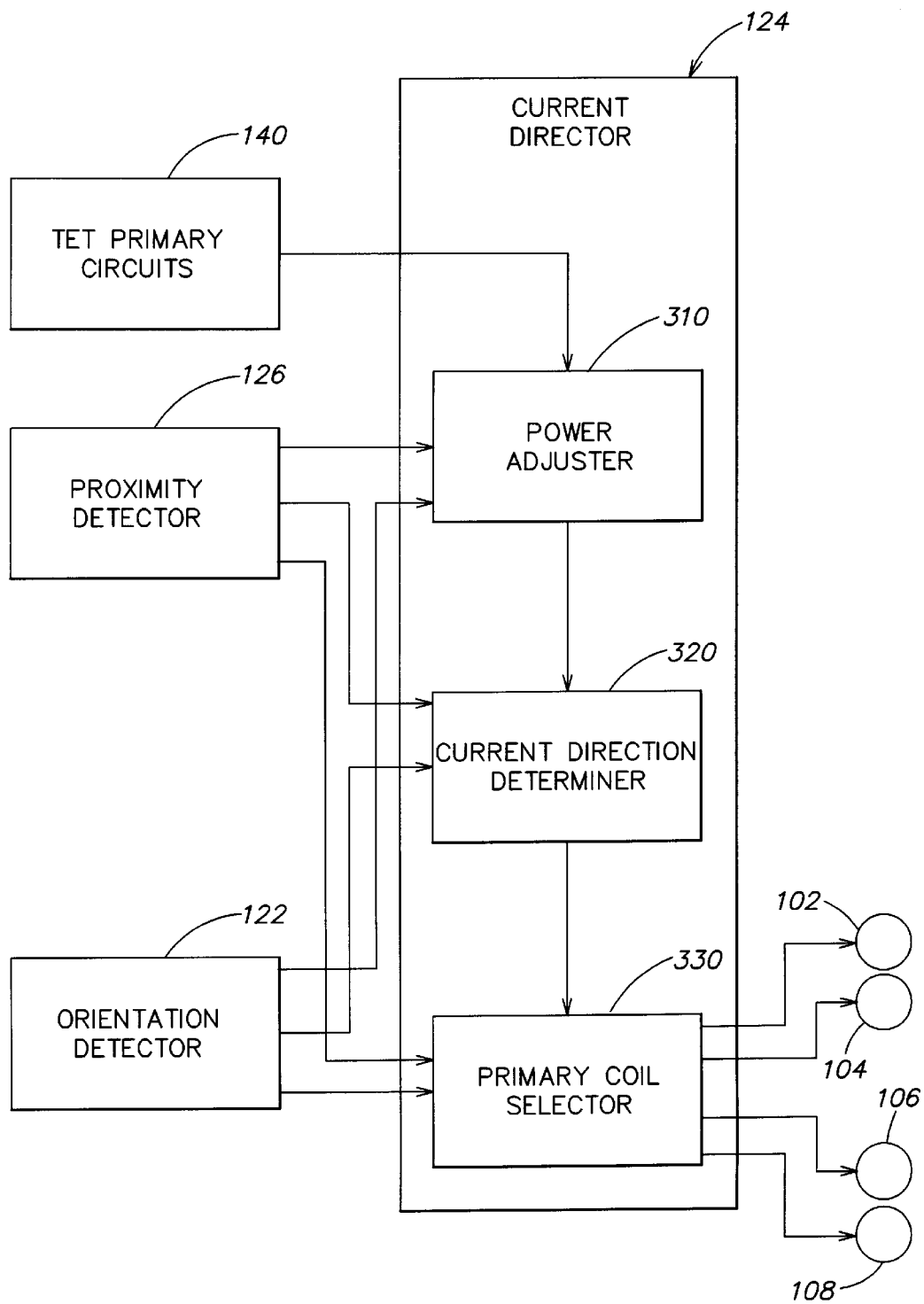
FIG. 3 is a functional block diagram of one embodiment of a current director of one embodiment of a controller of the electromagnetic field source of FIG. 1.

Primary coil selector 330 also typically employs any of a variety of known switching techniques and devices to direct current to the selected primary coils. For example, any of a large number of solid-state electronic switches, or mechanical switches, may be employed. In FIG. 3, this switching function is represented by the connection of primary coil selector 330 to connectors 102–108. As shown in FIG. 1, connectors 102 and 104 are respectively connected to the output and input terminals of primary coil 110A, and connectors 106 and 108 are similarly connected to primary coil 110B.

B. Proximity Detector

As noted, proximity detector 126 determines the one or more closest primary coils to secondary coil 230, and may also determine the location of secondary coil 230 with respect to the closest primary coils (i.e., between two coils, over the middle of one coil, over an external segment of one coil, and so on). For clarity and convenience, such information hereafter is simply referred to as the "proximity" or "closeness" of secondary coil 230. As is evident, the proximity of secondary coil 230 to various primary coils typically changes over time as recipient 205 moves. Thus, the identification of the closest primary coils may consequently change over time. It will thus be understood that the determinations made by proximity detector 126 (and by orientation detector 122, described below) typically are made at intervals, or they may be made essentially continuously. For example, if calculations and comparisons are made in an analog system, proximity detector 126 may process information continuously. If calculations and comparisons are made in a digital system using firmware, software, or a combination thereof, a period for making calculations may be determined in accordance with any of a variety of known techniques and in accordance with the time needed to execute the firmware or software.

In one embodiment, proximity detector 126 employs well known principles of mutual inductance to determine the proximity of secondary coil 230. Specifically, the inductances of each primary coil at a selected frequency, referred to as the "primary resonance frequency," are measured. This frequency may, but need not be, different than the frequency at which the alternating current changes direction (the "secondary resonance frequency"). The proximity of the secondary coil results in a mutual inductance that either adds to, or subtracts from, the inductance of the primary coil depending on the winding sense of the secondary compared to the primary. This change in the inductance of the primary coil being measured is referred to herein as a "frequency shift" because it changes the primary resonance frequency. As will be evident to those of ordinary skill in the relevant art, the mutual inductance of closely coupled primary and secondary coils is approximated by the following equation:

$$\frac{M}{L} = \frac{N_2}{N_1}\left(\frac{r_2}{r_1}\right)^2 \quad (2)$$

Where, M is the mutual inductance, L is the inductance of the primary coil without the secondary coil being present, $N_2$ and $N_1$ are the number of turns of the secondary and the primary coil, and $r_2$ and $r_1$ are the characteristic dimension of the secondary and primary coils, respectively. For typical values, such as provided in the illustrative example provided above with respect to the operation of power adjuster 310, $N_2$ equals 18 turns, $N_1$ equals 9 turns, $r_2$ equals 1.5 inches, and $r_1$ equals six inches. Thus, the ratio M/L is approximately equal to 0.125, or about 12 percent. That is, resonance frequency shifts of as much as approximately six percent in each direction, depending on the relative directions of windings, may be expected if secondary coil 230 is proximate to the primary coil being measured.

By thus measuring the proximity of each primary coil, the closest primary coils are determined. Similarly, it may be determined that a particular primary coil is the closest coil, but that the resonance shift is less than would be expected if the secondary coil were positioned at a nominal distance from the middle of the coil. Such reduced shift may be due to the secondary coil being between the measured primary coil and an adjacent primary coil, or at an edge of the measured coil nearer to the adjacent coil. Measurement of the frequency shift of the adjacent primary coil may confirm this.

Otherwise (i.e., if the proximity of the secondary coil to the adjacent primary coil is not as great as would be expected if the secondary coil were between the measured coil and the adjacent coil, or closer to the adjacent coil), the secondary coil may be at a greater-than-nominal distance above the measured primary coil. As will be evident to those skilled in the relevant arts, frequency shift information from the closest and adjacent primary coils may thus be used to determine the proximity and the location of the secondary coil.

Proximity detector 126 in this manner determines the proximity of each primary coil until one or more closest primary coils are identified or, alternatively, the mutual inductance of each primary coil is determined. One reason that it may be advantageous to measure all primary coils, even if it appears that one or more closest primary coils have been detected because of a significant frequency shift, is to avoid an erroneous determination due to the placement of a wire or other magnetically active material on or near mattress 210. Thus, for example, the distribution of inductance due to an electrical chord placed on the mattress typically will be different than the distribution of inductances due to the proximity of a secondary coil of the type typically implanted in recipient 205.

If all primary coils are measured and proximity detector 126 does not detect the proximity of secondary coil 230, then the measurement process may be repeated with more power provided to each primary coil. Optionally, if one or more closest primary coils are not detected, an alarm may be enabled in accordance with known techniques to indicate that the secondary coil is not being activated.

C. Orientation Detector 122

As previously described, orientation detector 122 determines whether secondary coil 230 is disposed in an orientation predominantly perpendicular, or alternatively, parallel, to the plane or planes of the primary coils. Such orientation is measured in the illustrated embodiment by detecting relative changes in the resonance shifts of adjacent primary coils.

For example, it is assumed that the primary coils are arranged in two parallel layers in accordance with the example of FIG. 10. It is also assumed that the frequency shift due to mutual inductance, as measured with respect to second-layer coil 1020A, is relatively high, and that the frequency shift with respect to first-layer coils 1010A and 1010B are approximately the same, and are relatively low as compared to that of coil 1020A. Thus, for the same reasons discussed above with respect to FIGS. 6B and 7B regarding the characteristics of magnetic fields, it is determined that secondary coil 230 is predominantly perpendicular with respect to the planes of coils 1010 and 1020, while being located at the edge of coil 1020A and equally divided between first-layer coils 1010A and 1010B.

As the differences decrease between the frequency shift of coil 1020A, on the one hand, and coils 1010A and 1010B, on the other hand, it may be determined that the predominance of the perpendicular orientation is decreasing; i.e., secondary coil 230 is becoming less perpendicular, and more parallel, to the planes of coils 1010 and 1020. If the relationship is reversed, such that the frequency shift of coil 1020A is relatively low in comparison to that of coils 1010A and 1010B, then it may be determined that secondary coil 230 is predominantly parallel to the planes of coils 1010 and 1020. Orientation detector 122 thus determines the orientation of secondary coil 230, within the range from predominantly perpendicular to predominantly parallel, with respect to the planes of the primary coils.

Having now described one embodiment of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments.

For example, numerous variations are contemplated in accordance with the present invention to carry out the functions of controller 120. The operations of orientation detector 122, or portions thereof, may be combined with those of proximity detector 126, or portions thereof. Similarly, either or both of detectors 122 and 126 may carry out the operations of current director 124, or vice versa.

Either, or both, of the detectors 122 and 126 may be implemented in alternative embodiments by mechanical, optical, electromagnetic transmission (e.g., implanting a radio-frequency transmitter with secondary coil 230 and detecting the strength and direction of its signal), or other detectors. Such detectors may be employed with, or instead of, the resonance frequency shift detectors described with respect to the illustrated embodiment.

Also, the division of functions of current director 124 into power adjuster 310, current direction determiner 320, and primary coil selector 330 is made for convenience of illustration and other distributions of these, and other, functions may be made in alternative embodiments. Also, as noted, many possible variations are possible with respect to the shape of primary coils, the number of loops in them, their orientations in planes with respect to each other and their housings, patterns in which arrays of primary coils are arranged, and other factors.

In addition, it will be understood by those skilled in the relevant art that control and data flows between and among functional elements of the invention may vary in many ways from the control and data flows described above. More particularly, intermediary functional elements (not shown) may direct control or data flows; the functions of various elements may be combined, divided, or otherwise rearranged to allow parallel processing or for other reasons; data structures may be employed to store and/or manipulate data; the sequencing of functions or portions of functions generally may be altered; and so on. Numerous other embodiments, and modifications thereof, are contemplated as falling within the scope of the present invention as defined by appended claims and equivalents thereto.

What is claimed is:

1. An electromagnetic field source for providing electromagnetic energy to a secondary coil, comprising:
   a plurality of primary coils, each constructed and arranged to carry a time-varying current to produce an electromagnetic field; and
   a controller constructed and arranged to detect a position and orientation of the secondary coil relative to one or more of the plurality of primary coils and to selectively provide current to one or more of the plurality of primary coils based on the position and orientation of the secondary coil relative to the primary coils.

2. The electromagnetic field source of claim 1, wherein the controller comprises:
   a proximity detector constructed and arranged to identify a quantity of the plurality of primary coils that are closest to the secondary coil; and
   a current director, responsive to the proximity detector and electrically coupled to the plurality of primary coils, constructed and arranged to selectively direct time-varying currents through the closest primary coils.

3. The electromagnetic field source of claim 2, wherein: the quantity of closest primary coils identified by the proximity detector is a predetermined value.

4. The electromagnetic field source of claim 2, wherein: the quantity of closest primary coils identified by the proximity detector is based on a size of the secondary coil.

5. The electromagnetic field source of claim 2, wherein: each primary coil is disposed in a plane substantially parallel to, including the same plane as, a plane of each of the other primary coils.

6. The electromagnetic field source of claim 5, wherein the primary coils are disposed in two or more substantially parallel planes, including:
   a first plane having one or more first-plane primary coils that, when energized, generate electromagnetic fields having one or more dead zones; and
   a second plane having at least one second-plane primary coil positioned with respect to the two or more mutually adjacent first-plane primary coils to generate, when energized, at least one electromagnetic field encompassing the one or more dead zones.

7. The electromagnetic field source of claim 5, wherein the primary coils are disposed in two or more substantially parallel planes, including:
   a first plane having two or more mutually adjacent first-plane primary coils; and
   a second plane having at least one second-plane primary coil positioned with respect to the two or more mutually adjacent first-plane primary coils so that the projection of a magnetic center of the second-plane primary coil on the first plane is approximately equidistant from magnetic centers of each of the two or more mutually adjacent first-plane primary coils.

8. The electromagnetic field source of claim 5, wherein the primary coils are disposed in two or more substantially parallel planes, including:
   a first plane having four mutually adjacent primary coils positioned with respect to each other in a roughly square arrangement; and
   a second plane having one primary coil positioned so that the projection of its geometric center on the first plane is approximately centrally located among the four first-plane primary coils.

9. The electromagnetic field source of claim 5, wherein the controller comprises:
   an orientation detector, coupled to the current director, constructed and arranged to determine the orientation of a plane that includes the secondary coil with respect to the planes of the closest primary coils.

10. The electromagnetic field source of claim 9, wherein: the orientation detector is electrically coupled to the plurality of primary coils and comprises a resonance frequency shift detector that compares shifts in inductance of two or more primary coils due to a proximity of the secondary coil.

11. The electromagnetic field source of claim 9, wherein: the orientation detector comprises an optical sensor.

12. The electromagnetic field source of claim 9, wherein: the orientation detector comprises an mechanical sensor.

13. The electromagnetic field source of claim 9, wherein: the orientation detector comprises an electromagnetic transmission sensor.

14. The electromagnetic field source of claim 9, wherein: the proximity detector, current director, and orientation detector are each implemented by at least one of a group of software, firmware, and electrical circuits.

15. The electromagnetic field source of claim 9, wherein: when the orientation detector determines that the secondary coil is disposed in a plane predominantly parallel to the planes of the closest primary coils, the current director directs time-varying currents to flow through the closest primary coils so that each current flows in a same direction.

16. The electromagnetic field source of claim 15, wherein: the quantity of closest primary coils is one when the proximity detector determines that the secondary coil is proximate to an electromagnetic field of the one closest primary coil, not including a dead zone.

17. The electromagnetic field source of claim 15, wherein: the quantity of closest primary coils is two or more when all of the plurality of primary coils are disposed in a same plane and the proximity detector determines that the secondary coil is proximate to a dead zone of a one closest primary coil.

18. The electromagnetic field source of claim 9, wherein:

when the orientation detector determines that the secondary coil is disposed in a plane predominantly perpendicular to the planes of the closest primary coils, the current director directs time-varying currents to flow through the closest primary coils so that a current in each closest primary coil flows in a direction opposite to a direction of a current in an adjacent closest primary coil.

19. The electromagnetic field source of claim 18, wherein:

the quantity of closest primary coils is two.

20. The electromagnetic field source of claim 2, wherein:

the proximity detector is electrically coupled to the plurality of primary coils and identifies the quantity of closest primary coils utilizing a resonance frequency shift detector that detects a shift in inductance of one or more primary coils due to a proximity of the secondary coil.

21. The electromagnetic field source of claim 2, wherein:

the proximity detector identifies the quantity of closest primary coils utilizing an optical sensor.

22. The electromagnetic field source of claim 2, wherein:

the proximity detector identifies the quantity of closest primary coils utilizing a mechanical sensor.

23. The electromagnetic field source of claim 2, wherein:

the proximity detector identifies the quantity of closest primary coils utilizing electromagnetic transmission.

24. The electromagnetic field source of claim 2, wherein:

the proximity detector is further constructed and arranged to determine an approximate distance between one or more of the closet primary coils and the secondary coil, and the current director is further constructed and arranged to increase the currents through the closest primary coils when the proximity detector determines that the distance is greater than a nominal threshold value.

25. The electromagnetic field source of claim 2, further comprising:

a power supply coupled to the current director and constructed and arranged to generate the current directed to the primary coils.

26. The electromagnetic field source of claim 1, further comprising:

one or more articles of furniture constructed and arranged to house the primary coils.

27. The electromagnetic field source of claim 26, wherein:

the furniture includes a bed.

28. The electromagnetic field source of claim 26, wherein:

the furniture includes at least one mattress having a top surface and the primary coils are positioned in the mattress.

29. The electromagnetic field source of claim 28, wherein:

the primary coils are disposed over substantially all of the top surface of the mattress.

30. The electromagnetic field source of claim 28, wherein:

the primary coils are positioned in generally even rows and columns with respect to the top surface of the mattress.

31. The electromagnetic field source of claim 28, wherein:

the primary coils are positioned in generally hexagonal arrangements with respect to the top surface of the mattress.

32. The electromagnetic field source of claim 1, further comprising:

a bed covering constructed and arranged to house the primary coils.

33. A method for providing electromagnetic energy to a secondary coil, comprising:

(1) providing an electromagnetic field source comprising a plurality of primary coils, each constructed and arranged to carry a time-varying current to produce an electromagnetic field, and a controller constructed and arranged to detect a position and orientation of the secondary coil relative to one or more of the plurality of primary coils and to selectively provide current to one or more of the plurality of primary coils based on the position and orientation of the secondary coil relative to the primary coils;

(2) detecting a position and orientation of one or more of the secondary coil relative to the plurality of primary coils by the controller; and (3) selectively providing current to one or more of the plurality of primary coils based on the position and orientation of the secondary coil relative to the primary coils by the controller.

34. The method of claim 33, wherein:

the controller comprises a proximity detector and a current director responsive to the proximity detector and electrically coupled to the plurality of primary coils;

detecting a position in step 2 comprises identifying a quantity of the plurality of primary coils that are closest to the secondary coil by the proximity detector; and selectively providing current in step 3 comprises selectively directing time-varying currents through the closest primary coils by the current director.

35. The method of claim 34, wherein:

the quantity of closest primary coils identified by the proximity detector is a predetermined value.

36. The method of claim 34, wherein:

the quantity of closest primary coils identified by the proximity detector is based on a size of the secondary coil.

37. The method of claim 34, wherein step 1 comprises:

providing each primary coil in a plane substantially parallel to, including the same plane as, a plane of each of the other primary coils.

38. The method of claim 37, wherein step 1 comprises providing the primary coils in two or more substantially parallel planes, including:

a first plane having one or more first-plane primary coils that, when energized, generate electromagnetic fields having one or more dead zones; and a second plane having at least one second-plane primary coil positioned with respect to the two or more mutually adjacent first-plane primary coils to generate, when energized, at least one electromagnetic field encompassing the one or more dead zones.

39. The method of claim 37, wherein step 1 comprises providing the primary coils in two or more substantially parallel planes, including:

a first plane having two or more mutually adjacent first-plane primary coils; and a second plane having at least one second-plane primary coil positioned with respect to the two or more mutually adjacent first-plane primary coils so that the projection of a magnetic center of the second-plane primary coil on the first plane is approximately equidistant from magnetic centers of each of the two or more mutually adjacent first-plane primary coils.

40. The method of claim 37, wherein step 1 comprises providing the primary coils in two or more substantially parallel planes, including:

a first plane having four mutually adjacent primary coils positioned with respect to each other in a roughly square arrangement; and a second plane having one primary coil positioned so that the projection of its geometric center on the first plane is approximately centrally located among the four first plane primary coils.

41. The method of claim 34, wherein:

the controller further comprises an orientation director; and detecting an orientation in step 2 further comprises determining the orientation of a plane that includes the secondary coil with respect to the planes of the closest primary coils by the orientation director.

42. The method of claim 41, wherein:

the orientation detector is electrically coupled to the plurality of primary coils and determines the orientation of the plane of the secondary coil utilizing a resonance frequency shift detector to compares shifts in inductance of two or more primary coils due to a proximity of the secondary coil.

43. The method of claim 41, wherein:

the orientation detector determines the plane of the secondary coil utilizing an optical sensor.

44. The method of claim 41, wherein:

the orientation detector determines the plane of the secondary coil utilizing a mechanical sensor.

45. The method of claim 41, wherein:

the orientation detector determines the plane of the secondary coil utilizing electromagnetic transmission.

46. The method of claim 41, wherein:

the proximity detector, current director, and orientation detector are each implemented by at least one of a group of software, firmware, and electrical circuits.

47. The method of claim 41, wherein:

when the orientation detector determines that the secondary coil is disposed in a plane predominantly parallel to the planes of the closest primary coils, the current director directs time-varying currents to flow through the closest primary coils so that each current flows in a same direction.

48. The method of claim 47, wherein:

the quantity of closest primary coils is one when the proximity detector determines that the secondary coil is proximate to an electromagnetic field of the one closest primary coil, not including a dead zone.

49. The method of claim 47, wherein:

the quantity of closest primary coils is two or more when all of the plurality of primary coils are disposed in a same plane and the proximity detector determines that the secondary coil is proximate to a dead zone of a one closest primary coil.

50. The method of claim 41, wherein:

when the orientation detector determines that the secondary coil is disposed in a plane predominantly perpendicular to the planes of the closest primary coils, the current director directs time-varying currents to flow through the closest primary coils so that a current in each closest primary coil flows in a direction opposite to a direction of a current in an adjacent closest primary coil.

51. The method of claim 50, wherein:

the quantity of closest primary coils is two.

52. The method of claim 43, wherein:

the proximity detector is electrically coupled to the plurality of primary coils and identifies the quantity of closest primary coils utilizing a resonance frequency shift detector that detects a shift in inductance of one or more primary coils due to a proximity of the secondary coil.

53. The method of claim 34, wherein:

the proximity detector identifies the quantity of closest primary coils utilizing an optical sensor.

54. The method of claim 34, wherein:

the proximity detector identifies the quantity of closest primary coils utilizing a mechanical sensor.

55. The method of claim 34, wherein:

the proximity detector identifies the quantity of closest primary coils utilizing electromagnetic transmission.

56. The method of claim 34, wherein:

the proximity detector is further constructed and arranged to determined an approximate distance between one or more of the closest primary coils and the secondary coil, and the current director is further constructed and arranged to increase the currents through the closest primary coils when the proximity detector determines that the distance is greater than a nominal threshold value.

57. The method of claim 33, further comprising:

providing the primary coils in one or more articles of furniture.

58. The method of claim 57, wherein:

the furniture includes a bed.

59. The method of claim 57, wherein:

the furniture includes at least one mattress having a top surface and the primary coils are positioned in the mattress.

60. The method of claim 59, wherein:

the primary coils are disposed over substantially all of the top surface of the mattress.

61. The method of claim 59, wherein:

the primary coils are positioned in generally even rows and columns with respect to the top surface of the mattress.

62. The method of claim 59, wherein:

the primary coils are positioned in generally hexagonal arrangements with respect to the top surface of the mattress.

63. The method of claim 33, further comprising:

providing the primary coils in a bed covering.

64. A system for providing electromagnetic energy to a secondary coil, comprising:

a plurality of primary coils, each constructed and arranged to carry a time-varying current to produce an electromagnetic field; and a controller means for detecting a position and orientation of the secondary coil relative to one or more of the plurality of primary coils and for selectively providing current to one or more of the plurality of primary coils based on the position and orientation of the secondary coil relative to the primary coils.

65. The system of claim 64, wherein the controller means comprises:

a proximity detector means for identifying a quantity of the plurality of primary coils that are closest to the secondary coil; and a current director means, responsive to the proximity detector means and electrically coupled to the plurality of primary coils, for selectively directing time-varying currents through the closest primary coils.

66. The system of claim 65, wherein:

the quantity of closest primary coils identified by the proximity detector means is a predetermined value.

67. The system of claim 65, wherein:

the quantity of closest primary coils identified by the proximity detector means is based on a size of the secondary coil.

68. The system of claim 65, wherein:

each primary coil is disposed in a plane substantially parallel to, including the same plane as, a plane of each of the other primary coils.

69. The system of claim 68, wherein the primary coils are disposed in two or more substantially parallel planes, including:

a first plane having one or more first-plane primary coils that, when energized, generate electromagnetic fields having one or more dead zones; and a second plane having at least one second-plane primary coil positioned with respect to the two or more mutually adjacent first-plane primary coils to generate, when energized, at least one electromagnetic field encompassing the one or more dead zones.

70. The system of claim 68, wherein the primary coils are disposed in two or more substantially parallel planes, including:

a first plane having two or more mutually adjacent first-plane primary coils; and a second plane having at least one second-plane primary coil positioned with respect to the two or more mutually adjacent first-plane primary coils so that the projection of a magnetic center of the second-plane primary coil on the first plane is approximately equidistant from magnetic centers of each of the two or more mutually adjacent first-plane primary coils.

71. The system of claim 68, wherein the primary coils are disposed in two or more substantially parallel planes, including:

a first plane having four mutually adjacent primary coils positioned with respect to each other in a roughly square arrangement; and a second plane having one primary coil positioned so that the projection of its geometric center on the first plane is approximately centrally located among the four first plane primary coils.

72. The system of claim 68, wherein the controller means comprises:

an orientation detector means, coupled to the current director means, for determining the orientation of a plane that includes the secondary coil with respect to the planes of the closest primary coils.

73. The system of claim 72, wherein:

the orientation detector means is electrically coupled to the plurality of primary coils and comprises a resonance frequency shift detector means for determining the orientation of the plane of the secondary coil by comparing shifts in inductance of two or more primary coils due to a proximity of the secondary coil.

74. The system of claim 72, wherein:

the orientation detector means comprises an optical sensor means for determining the plane of the secondary coil utilizing an optical sensor.

75. The system of claim 72, wherein:

the orientation detector means comprises a mechanical sensor means for determining the plane of the secondary coil.

76. The system of claim 72, wherein:

the orientation detector means comprises an electromagnetic transmission detector means for determining the plane of the secondary coil.

77. The system of claim 76, wherein:

the primary coils are positioned in generally hexagonal arrangements with respect to the top surface of the mattress.

78. The system of claim 72, wherein:

the proximity detector means, current director means, and orientation detector means are each implemented by at least one of a group of software, firmware, and electrical circuits.

79. The system of claim 72, wherein:

when the orientation detector means determines that the secondary coil is disposed in a plane predominantly parallel to the planes of the closest primary coils, the current director means directs time-varying currents to flow through the closest primary coils so that each current flows in a same direction.

80. The system of claim 79, wherein:

the quantity of closest primary coils is one when the proximity detector means determines that the secondary coil is proximate to an electromagnetic field of the one closest primary coil, not including a dead zone.

81. The system of claim 79, wherein:

the quantity of closest primary coils is two or more when all of the plurality of primary coils are disposed in a same plane and the proximity detector means determines that the secondary coil is proximate to a dead zone of a one closest primary coil.

82. The system of claim 72, wherein:

when the orientation detector means determines that the secondary coil is disposed in a plane predominantly perpendicular to the planes of the closest primary coils, the current director means directs time-varying currents to flow through the closest primary coils so that a current in each closest primary coil flows in a direction opposite to a direction of a current in an adjacent closest primary coil.

83. The system of claim 82, wherein:

the quantity of closest primary coils is two.

84. The system of claim 65, wherein:

the proximity detector means is electrically coupled to the plurality of primary coils and comprises a resonance frequency shift detector means for identifying the quantity of closest primary coils by detecting a shift in inductance of one or more primary coils due to a proximity of the secondary coil.

85. The system of claim 65, wherein:

the proximity detector means comprises an optical sensor means for identifying the quantity of closest primary coils.

86. The system of claim 65, wherein:

the proximity detector means comprises a mechanical sensor means for identifying the quantity of closest primary coils.

87. The system of claim 65, wherein:

the proximity detector means comprises an electromagnetic transmission detector means for identifying the quantity of closest primary coils.

88. The system of claim 65, wherein:

the proximity detector means is further constructed and arranged to determine an approximate distance between one or more of the closest primary coils and the secondary coil, and the current director means is further constructed and arranged to increase the currents through the closest primary coils when the proximity detector determines that the distance is greater than a nominal threshold value.

89. The system of claim 65, wherein the current director means includes a power adjuster means for adjusting the amount of current directed to the closest primary coils.

90. The system of claim 65, wherein the current director means includes a current direction determiner means for determining the directions of current supplied to two or more closest primary coils.

91. The system of claim 65, wherein the current director means includes a primary coil selector means for selecting primary coils to receive the current.

92. The system of claim 64, further comprising:

a power supply coupled to the current director means.

93. The system of claim 64, further comprising:

one or more articles of furniture constructed and arranged to house the primary coils.

94. The system of claim 93, wherein:

the furniture includes a bed.

95. The system of claim 93, wherein:

the furniture includes at least one mattress having a top surface and the primary coils are positioned in the mattress.

96. The system of claim 95, wherein:

the primary coils are disposed over substantially all of the top surface of the mattress.

97. The system of claim 95, wherein:

the primary coils are positioned in generally even rows and columns with respect to the top surface of the mattress.

98. The system of claim 64, further comprising:

a bed covering constructed and arranged to house the primary coils.

* * * * *

UNITED STATES PATENT AND TRADEMARK OFFICE
CERTIFICATE OF CORRECTION

PATENT NO. : 6,212,430 B1  
DATED : April 3, 2001  
INVENTOR(S) : Robert T.V. Kung Page 1 of 1

It is certified that error appears in the above-identified patent and that said Letters Patent is hereby corrected as shown below:

Column 25,
Line 14, "orientation director;" should read -- orientation detector; --.
Line 19, "orientation director." should read -- orientation detector. --.
Line 24, "detector to compares shifts" should read -- detector to compare shifts --.

Column 26,
Line 3, "method of claim 43" should read -- method of claim 34 --.

Signed and Sealed this

Fifth Day of March, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,212,430 B1
DATED        : April 3, 2001
INVENTOR(S)  : Robert T.V. Kung et al.

It is certified that error appears in the above-identified patent and that said Letters Patent is hereby corrected as shown below:

<u>Column 24,</u>
Lines 17-19, reads "detecting a position and orientation of one or more of the secondary coil relative to the plurality of primary coils by the controller; and" should read
-- detecting a position and orientation of the secondary coil relative to one or more of the plurality of primary coils by the controller; and --

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,212,430 B1
DATED : April 3, 2001
INVENTOR(S) : Robert T.V. Kung

It is certified that error appears in the above-identified patent and that said Letters Patent is hereby corrected as shown below:

Column 1,
Line 17, reads "cochler" should read -- cochlear --;

Column 4,
Line 43, reads "simple" should read -- simply --;

Column 10,
Line 10, reads "finction" should read -- function --;

Column 13,
Line 39, reads "830B and 830B" should read -- 830B and 830C --;

Column 17,
Line 15, reads "secondary coil 230" should read -- primary coil 1010 --;
Line 39, delete "in".

Signed and Sealed this

Thirtieth Day of December, 2003

JAMES E. ROGAN
*Director of the United States Patent and Trademark Office*